(12) United States Patent
Wakabayashi et al.

(10) Patent No.: US 11,841,335 B2
(45) Date of Patent: Dec. 12, 2023

(54) NONDESTRUCTIVE INSPECTION METHOD AND APPARATUS COMPRISING A NEUTRON SOURCE AND A GAMMA-RAY DETECTION DEVICE FOR DETERMINING A DEPTH OF A TARGET COMPONENT IN AN INSPECTION TARGET

(71) Applicant: RIKEN, Wako (JP)

(72) Inventors: Yasuo Wakabayashi, Wako (JP); Yoshie Otake, Wako (JP); Yujiro Ikeda, Wako (JP)

(73) Assignee: RIKEN, Wako (JP)

( * ) Notice: Subject to any disclaimer, the term of this patent is extended or adjusted under 35 U.S.C. 154(b) by 142 days.

(21) Appl. No.: 17/066,593

(22) Filed: Oct. 9, 2020

(65) Prior Publication Data

US 2021/0033542 A1 Feb. 4, 2021

Related U.S. Application Data

(63) Continuation-in-part of application No. PCT/JP2018/038074, filed on Oct. 12, 2018.

(30) Foreign Application Priority Data

Apr. 12, 2018 (JP) .................................. 2018-076651

(51) Int. Cl.
*G01N 23/222* (2006.01)
*G01V 5/00* (2006.01)
(Continued)

(52) U.S. Cl.
CPC ......... *G01N 23/222* (2013.01); *G01N 23/025* (2013.01); *G01N 23/22* (2013.01);
(Continued)

(58) Field of Classification Search
CPC .... G01N 23/22; G01N 23/221; G01N 23/222; G01V 5/0016; G01V 5/0069
(Continued)

(56) References Cited

U.S. PATENT DOCUMENTS 3,025,399 A * 3/1962 Verbinski ............. G01N 23/222
376/159
3,247,381 A * 4/1966 Caldwell ................ G01V 5/101
250/269.6
(Continued)

FOREIGN PATENT DOCUMENTS

JP 1995294652 A 11/1995
JP 1995301610 A 11/1995
(Continued)

OTHER PUBLICATIONS

An English translation of JPH07301610A by Patent Translate. (Year: 2022).*
(Continued)

*Primary Examiner* — Allen C. Ho
(74) *Attorney, Agent, or Firm* — Volpe Koenig

(57) ABSTRACT

A nondestructive inspection apparatus makes a neutron beam incident on an inspection target, detects a specific gamma ray deriving from a target component in the inspection target, among gamma rays generated by the neutron beam, and determines a depth at which the target component exists, based on a result of the detecting. The nondestructive inspection apparatus includes a neutron source that emits a neutron beam to a surface of the inspection target, a gamma ray detection device that detects, as detection intensities, intensities of a plurality of types of specific gamma rays whose energy differs from each other, and a ratio calculation unit that determines a ratio between the detection intensities of a plurality of types of the specific gamma rays.

16 Claims, 17 Drawing Sheets

(51) Int. Cl.
  *G01N 23/02* (2006.01)
  *G01T 1/16* (2006.01)
  *G01N 23/221* (2006.01)
  *G01N 23/22* (2018.01)

(52) U.S. Cl.
  CPC ............. *G01N 23/221* (2013.01); *G01T 1/16* (2013.01); *G01V 5/0016* (2013.01); *G01V 5/0069* (2016.11); *G01N 2223/03* (2013.01); *G01N 2223/1013* (2013.01); *G01N 2223/1063* (2013.01); *G01N 2223/1066* (2013.01); *G01N 2223/60* (2013.01)

(58) Field of Classification Search
  USPC .................... 376/157–159, 161, 163, 165
  See application file for complete search history.

(56) References Cited

U.S. PATENT DOCUMENTS

| | | | | | |
|---|---|---|---|---|---|
| 3,413,471 | A | * | 11/1968 | Tittman | G01V 5/102 376/165 |
| 3,508,052 | A | * | 4/1970 | Seevers | G01V 5/102 250/362 |
| 3,733,486 | A | * | 5/1973 | Arnold | G01V 5/102 250/389 |
| 3,780,301 | A | * | 12/1973 | Smith, Jr. | G01V 5/102 250/269.6 |
| 3,780,302 | A | * | 12/1973 | Arnold | G01V 5/102 250/269.6 |
| 3,925,659 | A | * | 12/1975 | Paap | G01V 5/102 376/163 |
| 4,020,342 | A | * | 4/1977 | Smith, Jr. | G01V 5/102 250/262 |
| 5,053,620 | A | * | 10/1991 | McKeon | G01V 5/06 250/269.7 |
| 5,412,206 | A | | 5/1995 | Seidel | |
| 5,539,788 | A | | 7/1996 | Ruddy | |
| 6,518,579 | B1 | * | 2/2003 | Xu | G01T 1/169 250/393 |
| 6,825,459 | B2 | * | 11/2004 | Bothner | G01V 5/125 250/269.1 |
| 6,936,812 | B2 | * | 8/2005 | Odom | G01V 5/104 250/269.4 |
| 7,566,869 | B2 | * | 7/2009 | Riley | G01V 5/125 250/269.6 |
| 7,573,044 | B2 | * | 8/2009 | Norris | G01V 5/0069 250/390.04 |
| 8,080,808 | B2 | * | 12/2011 | Norris | G01V 5/0008 250/390.04 |
| 8,680,477 | B2 | * | 3/2014 | Nose | G01N 23/222 250/269.6 |
| 8,785,864 | B2 | * | 7/2014 | Ricci | H01L 27/14663 250/367 |
| 8,996,315 | B2 | * | 3/2015 | Guo | G01N 33/24 250/269.3 |
| 9,170,218 | B2 | * | 10/2015 | Naqvi | G01V 5/0069 |
| 9,255,899 | B2 | * | 2/2016 | Nose | G01N 23/222 |
| 9,304,214 | B2 | * | 4/2016 | Zhou | G01T 3/06 |
| 10,126,257 | B2 | * | 11/2018 | Silarski | G01V 5/0016 |
| 10,161,237 | B2 | * | 12/2018 | Han | E21B 47/11 |
| 10,458,930 | B2 | * | 10/2019 | Torbert, III | G01T 1/169 |
| 10,527,752 | B2 | * | 1/2020 | Fox | G01V 5/14 |
| 10,690,802 | B2 | * | 6/2020 | Stoller | E21B 33/14 |
| 2002/0150194 | A1 | | 10/2002 | Wielopolski et al. | |
| 2012/0199746 | A1 | | 8/2012 | Nose | |
| 2012/0199754 | A1 | | 8/2012 | Nose | |
| 2014/0346366 | A1 | | 11/2014 | Naqvi et al. | |

FOREIGN PATENT DOCUMENTS

| | | |
|---|---|---|
| JP | 2004125570 A | 4/2004 |
| JP | 2011085480 A | 4/2011 |
| JP | 2011085481 A | 4/2011 |
| JP | 2016045124 A | 4/2016 |

OTHER PUBLICATIONS

Mohamad Al-Sheikhly, Amde M. Amde, and Richard A. Livingston, Development of a 2nd Generation Neutron-Based Detector for Chloride in Concrete, Final Report for Highway IDEA Project 136, Transportation Research Board of the National Acedemies, Jul. 16, 2014. (Year: 2014).*
Yamada, K. 2008, vol. 30, No. 2, pp. 757-762.
Yamada, K. Jul. 2009, vol. 31, No. 1, pp. 1981-1986.
International Search Report issued in corresponding International Patent Application No. PCT/JP2018/038074 dated Dec. 25, 2018, consisting of 17 pp.
Extended European Search Report dated May 10, 2021 for European Patent Application No. 18914496.7.
Japanese Office Action dated Oct. 21, 2022 for Japanese Patent Application No. 2020-513057.
Communication pursuant to Article 94(3) EPC dated Mar. 3, 2023 for European Patent Application No. 18914496.7.
Japanese Office Action dated Mar. 3, 2023 for Japanese Patent Application No. 2020-513057.

* cited by examiner

NONDESTRUCTIVE INSPECTION METHOD AND APPARATUS COMPRISING A NEUTRON SOURCE AND A GAMMA-RAY DETECTION DEVICE FOR DETERMINING A DEPTH OF A TARGET COMPONENT IN AN INSPECTION TARGET

This application is a continuation of International Patent Application No. PCT/JP2018/038074 filed on Oct. 12, 2018, which is incorporated by reference herein as fully set forth.

TECHNICAL FIELD

The present invention relates to a nondestructive inspection method and apparatus for nondestructively determining a depth of a position where a target component exists in an inspection target, and a concentration of the target component at the depth.

BACKGROUND ART

Damage due to chlorine (chloride ions) is one of factors causing deterioration of infrastructures such as a road and a bridge. For example, chlorine contained in a sea breeze from a coast, or chlorine contained in an antifreezing agent applied in a cold area or a mountain area infiltrates into a concrete structure as an infrastructure. Then, when a concentration (hereinafter, referred to as a chloride ion concentration) of chloride ions around a reinforcing steel bar in the concrete structure exceeds a limit value (a value in a range of 1.2 kg/m$^3$ to 2.5 kg/m$^3$), corrosion of the reinforcing steel bar occurs and progresses, causing the concrete structure to be deteriorated.

In order to maintain safety of a concrete structure, inspection is performed to grasp a deterioration state of the concrete structure. According to inspection of the prior art, at one location in the concrete structure, a concrete (referred to as a core) that exists in a range from the surface to the vicinity of the reinforcing steel bar is cut out, and the cut-out core is subjected to fluorescent X-ray analysis, electron probe microanalysis, potentiometric titration, or the like to measure a chloride ion concentration. In this manner, a chloride ion concentration is measured at each position in a range from the surface to a depth near the reinforcing steel bar in the concrete structure, and a deterioration condition of the concrete structure can be grasped.

CITATION LIST

Patent Literatures

PTL 1: Japanese Patent Application Laid-Open No. 2004-125570

SUMMARY OF INVENTION

Technical Problem

However, in extracting a core and measuring a chloride ion concentration thereof, there are the following problems (1) to (3). (1) A part of a concrete structure is damaged to extract the core, and thus, a location of the core extraction is limited. (2) It takes time to extract the core and perform pre-processing of measurement. (3) After a chloride ion concentration is measured for the core extracted from one location in the concrete structure, a chloride ion concentration cannot be measured for the same location. Thus, a change over the years in a deterioration condition of the same location cannot be grasped.

PTL 1 describes a technique of calculating a chloride ion concentration in a concrete, using an electromagnetic wave, but does not disclose that a depth of a position where chlorine exists is determined.

Thus, there is desired a technique capable of nondestructively detecting a depth of a position of a target component (e.g., chlorine) existing in an inspection target.

In view of it, an object of the present invention is to provide a technique capable of detecting a depth of a position of a target component existing in an inspection target without destruction of the inspection target, and a technique capable of evaluating a concentration of the target component at the depth.

Solution to Problem

A nondestructive inspection method according to one aspect of the present invention includes:

(A) making a neutron beam incident on an inspection target;

(B) detecting and identifying a specific gamma ray deriving from a target component in the inspection target, among gamma rays generated by the neutron beam; and (C) based on a result of the detecting, generating an index value indicating a depth at which the target component exists, wherein a step of (B) includes detecting, as detection intensities, intensities of a plurality of types of specific gamma rays whose energy differs from each other, and a step of (C) includes determining, as the index value, a ratio between the detection intensities of the plurality of types of specific gamma rays.

A nondestructive inspection apparatus according to one aspect of the present invention is an apparatus for making a neutron beam incident on an inspection target, detecting and identifying a specific gamma ray deriving from a target component in the inspection target, among gamma rays generated by the neutron beam, and determining a depth at which the target component exists, based on a result of the detecting, the nondestructive inspection apparatus including:

a neutron source that emits a neutron beam to a surface of the inspection target;

a gamma ray detection device that detects, as detection intensities, intensities of a plurality of types of specific gamma rays whose energy differs from each other; and a ratio calculation unit that determines a ratio between the detection intensities of the plurality of types of specific gamma rays.

A nondestructive inspection method according to another aspect of the present invention includes:

(A) making a pulse neutron beam incident on an inspection target;

(B) detecting a specific gamma ray deriving from a target component in the inspection target, among gamma rays generated by the pulse neutron beam; and (C) based on a result of the detecting, specifying, in relation to a reference time point, a time point at which the specific gamma ray is detected at (B).

A nondestructive inspection apparatus according to another aspect of the present invention is an apparatus for making a pulse neutron beam incident on an inspection target, detecting and identifying a specific gamma ray deriving from a target component in the inspection target, among gamma rays generated by the pulse neutron beam, and determining a depth at which the target component exists, based on a result of the detecting, the nondestructive inspection apparatus including:

a neutron source that emits a pulse neutron beam to a surface of the inspection target;

a gamma ray detection device that detects the specific gamma ray generated by the pulse neutron beam incident on the inspection target; and a time-point specifying unit that specifies, in relation to a reference time point, a time point at which the specific gamma ray is detected.

A nondestructive inspection method according to another aspect of the present invention is a method for making a neutron beam from a neutron source enter an inspection target, detecting and identifying a specific gamma ray deriving from a target component in the inspection target, among gamma rays generated by the neutron beam, and determining a depth at which the target component exists, based on a result of the detecting, the nondestructive inspection including:

(A) preparing a gamma ray detection device, wherein the gamma ray detection device includes a gamma ray detector that detects the specific gamma ray and a gamma ray shielding portion, a gamma ray passage hole is formed in the gamma ray shielding portion, the gamma ray passage hole includes an opening through which gamma rays are allowed to enter, the gamma ray detector is arranged in the gamma ray passage hole so as to be at a position shifted to a deep side from the opening, and the opening and the gamma ray detector are positioned on a reference straight line;

(B) arranging the neutron source, the gamma ray detector, and the gamma ray shielding portion such that a path of a neutron beam emitted from the neutron source and an extension line of the reference straight line intersects with each other inside the inspection target;

(C) in a state of (B), making a neutron beam from the neutron source enter the inspection target, and detecting thereby-generated gamma rays by the gamma ray detector; and (D) determining the number of times of detection of the specific gamma ray, based on detection data acquired by the gamma ray detector acquired at (C).

A nondestructive inspection apparatus according to another aspect of the present invention is an apparatus for making a neutron beam incident on an inspection target, detecting and identifying a specific gamma ray deriving from a target component in the inspection target, among gamma rays generated by the neutron beam, and determining a depth at which the target component exists, based on a result of the detecting, the nondestructive inspection apparatus comprising:

a neutron source that emits a neutron beam to a surface of the inspection target; and a gamma ray detection device that detects a specific gamma ray generated by the neutron beam incident on inspection target, wherein the gamma ray detection device includes a gamma ray detector for detecting the specific gamma ray, and a gamma ray shielding portion, and a gamma ray passage hole is formed in the gamma ray shielding portion, the gamma ray passage hole includes an opening through which gamma rays are allowed to enter, the gamma ray detector is arranged in the gamma ray passage hole so as to be at a position shifted to a deep side from the opening, and the opening and the gamma ray detector are positioned on a reference straight line.

Advantageous Effects of Invention

According to the present invention, without destruction of an inspection target, it is possible to detect a depth of a target component existing in the inspection target, and evaluate a concentration of the target component at the depth.

DESCRIPTION OF EMBODIMENTS

Embodiments of the present invention are described with reference to the drawings. The same reference symbols are attached to the parts that are common in the respective drawings, and overlapping description is omitted. The following description does not limit the invention described in claims. For example, the present invention is not limited to one including all of the constituent elements described below.

First Embodiment

Figure 1:
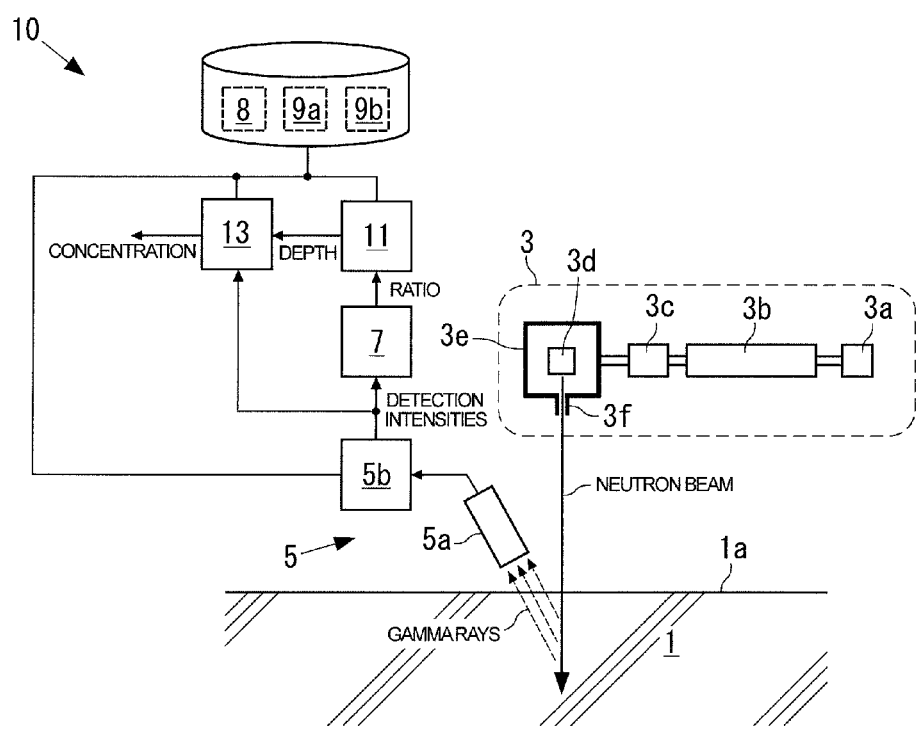
FIG. 1 illustrates a configuration of a nondestructive inspection apparatus according to a first embodiment of the present invention.

FIG. 1 illustrates a configuration of a nondestructive inspection apparatus 10 according to a first embodiment of the present invention. The nondestructive inspection apparatus 10 is an apparatus for emitting a neutron beam from an outside of an inspection target 1 to a surface 1a thereof, detecting and identifying, among gamma rays generated in the inspection target 1 by the neutron beam, a gamma ray (hereinafter, simply referred to also as a specific gamma ray) that derives from a target component in the inspection target 1, and determining a depth where the target component exists, on the basis of the detection result. Note that a depth of the target component is a depth from the surface 1a of the inspection target 1.

In an embodied example, the inspection target 1 is a concrete structure that includes reinforcing steel bars in the inside thereof, and the target component is chlorine (or chloride ions). When the target component is chlorine, the chlorine may be the stably existing isotope $^{35}Cl$ of chlorine Cl, for example. Note that the inspection target 1 and the target component are not limited to the combination of the concrete structure and chlorine. In other words, according to the first embodiment, the inspection target 1 is not limited to a concrete structure, and the target component may be any component that emits a plurality of types of specific gamma rays by a neutron beam made incident on the inspection target 1. For example, the target component may be calcium ($^{40}Ca$ as a majority), silicon ($^{28}Si$ as a majority), or the like. Note that hydrogen ($^{1}H$) emits only one type of gamma rays, and is thus inappropriate for the target component in the first embodiment, but in the second and third embodiments described later, hydrogen may be a target component.

As illustrated in FIG. 1, the nondestructive inspection apparatus 10 includes a neutron source 3, a gamma ray detection device 5, a ratio calculation unit 7, a depth data storage unit 9a, a depth detection unit 11, and a concentration data storage unit 9b.

The neutron source 3 emits a neutron beam to the surface 1a of the inspection target 1, making the neutron beam incident on the inspection target 1. The neutron source 3 may emit a pulse neutron beam, or may continuously emit a neutron beam. In the example of FIG. 1, the neutron source 3 includes an ion source 3a, an acceleration device 3b, a beam adjuster 3c, a target 3d, a container 3e, and a tubular shielding member 3f.

The ion source 3a generates hydrogen ions (protons), for example. The acceleration device 3b accelerates the protons generated by the ion source 3a. In one example, the protons accelerated by the acceleration device 3b each have energy of 7 MeV, for example. The beam adjuster 3c includes a plurality of magnetic field coils that adjust, to the target 3d, a direction and an area of the proton beam accelerated by the acceleration device 3b. The proton beam that has passed through the beam adjuster 3c is incident on the target 3d. As a result, reaction between the protons and the target 3d (e.g., beryllium) generates neutrons. The target 3d is arranged in the container 3e formed of a material hard to transmit neutrons and gamma rays. In the container 3e, there is formed a hole penetrating from the outer surface to the inside of the container 3e. To this hole, the tubular shielding member 3f for neutron emission is attached. The tubular shielding member 3f is formed of a material hard to transmit neutrons. Neutrons generated at the target 3d pass through the inside of the tubular shielding member 3f, and thereby form into a neutron beam to be incident on the inspection target 1.

Such a neutron source 3 can be configured in a small size enough to be loaded on a vehicle such as a truck. Accordingly, the above-described nondestructive inspection apparatus 10 can be loaded on a vehicle such as a truck, and be transported to a place where the inspection target 1 (e.g., an infrastructure such as a road or a bridge) exists.

In the first embodiment, a neutron beam emitted by the neutron source 3 may include thermal neutrons and fast neutrons. Generally, thermal neutrons indicate neutrons having energy nearly at 25 meV and neutrons having energy lower than 25 meV in the case of a room temperature, and fast neutrons indicate neutrons having energy (equal to or higher than several hundred keV) sufficiently higher than that of a thermal neutron. Here, there is no strict definition on thresholds for the names of neutrons based on energy, and for this reason, in the definition of the present application, thermal neutrons may be neutrons having energy equal to or lower than several ten meV (e.g., 50 meV), and fast neutrons may be neutrons having energy equal to or higher than several hundred keV (e.g., 200 keV). Note that a neutron having energy between that of a thermal neutron and that of a fast neutron may be referred to as an epithermal neutron, and a neutron having energy equal to or lower than 0.01 eV may be referred to as a cold neutron.

Figure 2:
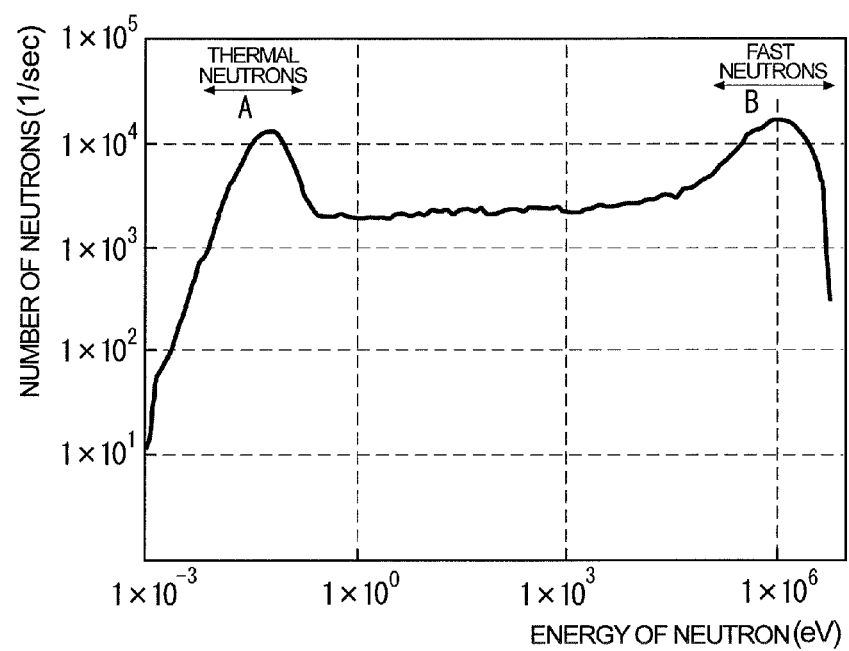
FIG. 2 illustrates one example of an energy spectrum of a neutron beam emitted from a neutron source.

Energy of respective neutrons emitted from the neutron source 3 has distribution of $1\times10^{-3}$ eV to $1\times10^{7}$ eV, for example, but may be set to be appropriate values depending on a type of inspection target 1. FIG. 2 illustrates one example of an energy spectrum of a neutron beam emitted from the above-described neutron source 3. In FIG. 2, the horizontal axis indicates energy (kinetic energy) of a neutron, and the vertical axis indicates the number of neutrons passing through a unit cross sectional area (one $cm^2$) in unit time (one second). According to the above-described definition in the present application, in FIG. 2, neutrons having energy in the range A are thermal neutrons, and neutrons having energy in the range B are fast neutrons.

The neutron beam made incident on the inspection target 1 by the neutron source 3 reacts with the target component in the inspection target 1. This generates specific gamma rays deriving from the target component. In the first embodiment, a plurality of types of specific gamma rays are generated from the target component, with energy values of the specific gamma rays being different between a plurality of the types.

The gamma ray detection device 5 detects, as detection intensities, intensities of specific gamma rays belonging to a plurality of the types generated by incidence of the neutron beam on the inspection target 1. The gamma ray detection device 5 includes a gamma ray detector 5a and an intensity detection unit 5b.

The gamma ray detector 5a detects gamma rays for each value of energy (each wavelength) of gamma rays from the inspection target 1, and inputs the detection data thereof to the intensity detection unit 5b. The detection data may indicate a pulse height corresponding to energy of each detected gamma ray.

The intensity detection unit 5b acquires an energy spectrum of gamma rays, based on each pulse height input from the gamma ray detector 5a. This energy spectrum indicates, at each energy value of gamma rays, the number of times of detection of the gamma ray. In the present application, the detection intensity of gamma rays may be a value proportional to the number of times of detection of the gamma ray having the corresponding energy value. The number of times of detection may be the number of times of detection over predetermined measurement time in the first embodiment. The predetermined measurement time is a time period from a time point as the origin when a neutron beam is emitted to the inspection target 1 to a time point when a sufficient amount of gamma rays caused by the neutron beam are detected by the gamma ray detector 5a. For example, the predetermined measurement time may be a time period of 100 seconds, 200 seconds, or 300 seconds from the above-mentioned origin, but is not limited to these time periods. In addition, the detection intensity of the gamma rays may be a count rate $R_y$ described later. The gamma ray detector 5a may be constituted by a germanium detector, for example, but is not limited to this.

The intensity detection unit 5b determines, as detection intensities, intensities of a plurality of types of the specific gamma rays (e.g., in the energy spectrum), based on the determined energy spectrum, and inputs these detection intensities to the ratio calculation unit 7. On the assumption that among a plurality of types of the specific gamma rays, one type of the specific gamma ray is a first specific gamma ray, and another type of the specific gamma ray is a second specific gamma ray, the intensity detection unit 5b may detect intensities of the first specific gamma rays and the second specific gamma rays, as respective detection intensities, and may input these detection intensities to the depth detection unit 11 and the concentration evaluation unit 13.

In an embodied example, a plurality of types of specific gamma rays deriving from $^{35}Cl$ as the target component include gamma rays having energy of 517 keV, 786 keV, 788 keV, 1165 keV, 1951 keV, and 6111 keV. In this case, for example, the first specific gamma ray may be the gamma ray having energy of 1951 keV, and the second specific gamma ray may be the gamma ray having energy of 517 keV. However, a combination of the first specific gamma ray and the second specific gamma ray is not limited to this. As an energy difference between the first specific gamma ray and the second specific gamma ray becomes larger, depth detection accuracy tends to become higher. However, use of a detection intensity of specific gamma rays having high energy (e.g., 6111 keV) may be avoided.

The ratio calculation unit 7 calculates a ratio between detection intensities of a plurality of types of the specific gamma rays input from the intensity detection unit 5b. In an embodied example, the ratio calculation unit 7 calculates a ratio of a detection intensity of the second specific gamma ray to a detection intensity of the first specific gamma ray.

The depth data storage unit 9a stores depth data representing a relation between a depth at which the target component exists in the inspection target 1 and a ratio between detection intensities of a plurality of types of the specific gamma rays. The depth data may be acquired in advance, and may be acquired by an experiment, for example.

In this experiment, a plurality of specimens formed of the same material as that of the inspection target 1 are prepared. Depths at which the target component exists in a plurality of the specimens differ among these specimens. A ratio between detection intensities of a plurality of the specific gamma rays is determined for each specimen, using the above-described neutron source 3 and gamma ray detection device 5. The above-described depth data are produced based on the depth of the target component in each of a plurality of the specimens and the above-described ratio for each of a plurality of the specimens. The thus-produced depth data are stored in advance in the depth data storage unit 9a. In an embodied example, the depth data represent a relation between a depth at which the target component exists in the inspection target 1 and a ratio of an intensity of the second specific gamma rays to an intensity of the first specific gamma rays.

Note that the above-described experiment for acquiring the depth data and actual inspection on the inspection target 1 (the step S1 described later) may be performed under the same conditions. The conditions include a neutron spectrum condition, a distance condition, and an orientation condition. The neutron spectrum condition is a condition that an energy spectrum of a neutron beam emitted from the neutron source 3 to the inspection target 1 (the specimen in the above-described experiment) is a set spectrum. The distance condition is a condition that a distance between the surface of the inspection target 1 (the specimen in the above-described experiment) and the detector 5a is a set distance. The orientation condition is a condition that a relation (an incident angle) between an orientation of a neutron beam emission port (in FIG. 1, an opening at a front end of the tubular shielding member 3f) in the neutron source 3 and an orientation of the surface 1a of the inspection target 1 (the specimen in the above-described experiment) is a set relation, and a relation between an orientation of the detector 5a and an orientation of the surface 1a of the inspection target 1 (detection angle) is a set relation (e.g., the incident angle is 90 degrees, and the detection angle is 45 degrees). The above-described "same conditions" may further include other conditions (e.g., a measurement time condition). The measurement time condition is a condition that the above-described measurement time is set time.

The depth detection unit 11 determines a depth at which the target component exists, based on the depth data stored in the depth data storage unit 9a and a ratio calculated by the ratio calculation unit 7. At this time, the depth detection unit 11 may apply the ratio to the depth data, and thereby determines a depth at which the target component exists. The depth detection unit 11 outputs the determined depth. The output depth may be stored in an appropriate storage medium, be displayed on a display, or be printed on a paper sheet.

Assuming that one of the first specific gamma ray and the second specific gamma ray is set as a selection gamma ray, the concentration data storage unit 9b stores concentration data representing a relation between a detection intensity of the selection gamma ray and a concentration of the target component. The concentration data storage unit 9 b stores the concentration data for each depth in the inspection target 1 so as to be associated with the depth. The concentration data may be acquired in advance, and may be acquired by an experiment, for example.

In this experiment, the following steps (1) to (3) are performed.
(1) A specimen is prepared. The specimen (referred to as a known-concentration specimen) is formed of the same material as that of the inspection target 1, and contains the target component at a known concentration.
(2) On the known-concentration specimen, a zero-concentration specimen is placed without a gap in a direction of thicknesses of both thereof. Here, the zero-concentration specimen is a specimen formed of the same material as that of the inspection target 1 and containing the target component at a concentration of zero. Each of the specimens has a rectangular parallelepiped shape.

(3) In the state of the step (2), the neutron source 3 emits a neutron beam such that the neutron beam passes through the zero-concentration specimen and the known-concentration specimen in this order, and a detection intensity of the thus-generated selection gamma rays is acquired by the gamma ray detection device 5.

The above-described steps (1) to (3) are performed for each of a plurality of known-concentration specimens whose concentrations of the target component are different from each other. Thereby, the above-described concentration data are produced based on the concentration of the target component in each of a plurality of the known-concentration specimens and the detection intensity of the selection gamma rays for each of a plurality of the known-concentration specimens. Here, the detection intensity may be acquired by the following equation (A). Each symbol in the equation (A) is the same as that in the case of the equation (1) described later. The equation (A) is an equation when $\varepsilon_\gamma$ in the below-described equation (1) is eliminated, i.e., when $\varepsilon_\gamma$ is set as "1".

$$R_\gamma = \{(A/t)/I_\gamma\}/(I_p/50) \quad (A)$$

A distance to the known-concentration specimen from a surface that belongs to the zero-concentration specimen and on which the neutron beam is made incident corresponds to a depth (a depth from the surface $1a$) in the inspection target 1. Thus, the concentration data acquired as described above for the one zero-concentration specimen (i.e., a thickness of this specimen) are data for one depth in the inspection target 1. For this reason, the concentration data are acquired as described above for each of a plurality of zero-concentration specimens whose thicknesses are different from each other. Thereby, the concentration data are acquired for each depth in the inspection target 1.

Alternatively, using a standard gamma ray source (e.g., $^{133}$Ba or $^{152}$Eu) for example, detection efficiency $\varepsilon_\gamma$ (described later) may be acquired in advance for each depth, and for each depth, the concentration data based on the detection efficiency for the depth may be acquired. In this case, at the above-described step (3), a detection intensity of the selection gamma rays is acquired by the below-described equation (1).

Note that the concentration data of depths (thicknesses of zero-concentration specimens) or the selection gamma ray (energy of the gamma ray) for which the experiment is not performed may be acquired by interpolation based on the concentration data or the detection efficiency for which the experiment is performed.

Note that the depth data storage unit $9a$, the concentration data storage unit $9b$, and the below-described detection efficiency storage unit 8 may be different storage areas in the same storage device such as a semiconductor memory, a hard disk, or a USB memory as illustrated in FIG. 1, or may be separate storage devices.

Based on a depth determined by the depth detection unit 11, the concentration data stored in the concentration data storage unit $9b$ and associated with this depth, and an input detection intensity of the selection gamma rays, the concentration evaluation unit 13 determines a concentration of the target component at this depth. At this time, the concentration evaluation unit 13 may apply the detection intensity of the selection gamma rays to the concentration data that are associated with the depth determined by the depth detection unit 11 and that are included in the concentration data associated with respective depths in the concentration data storage unit $9b$, and may thereby determine a concentration of the target component at this depth. The concentration evaluation unit 13 outputs the acquired concentration. The output concentration may be stored in an appropriate storage medium, be displayed on a display, or be printed on a paper sheet.

Note that the above-described experiment for acquiring the concentration data and the actual inspection (actual inspection at the time of acquiring a detection intensity of the selection gamma rays used at the below-described step S5 (the below-described steps S105 and S205 in the second embodiment and the third embodiment)) is performed under the same conditions. The conditions include the above-described neutron spectrum condition, distance condition, and orientation condition. Note that the "same conditions" may further include another condition (e.g., the above-described measurement time condition). A beam diameter of a neutron beam emitted by the neutron source 3 in the above-described experiment is the same as that in the actual inspection of the inspection target 1 because of the configuration of the neutron source 3 (e.g., the tubular shielding member $3f$) for example.

(Detection Principle of Depth of Target Component)
<Gamma Rays Deriving from Target Component>

The detection principle of a depth of the target component according to the first embodiment is described in detail. When a neutron beam is made incident on the inspection target 1, various elements existing in the inspection target 1 make reaction of capturing the neutrons, and become excited compound nuclei. The compound nuclei immediately transition from the excited state to a ground state, and at this time, emit gamma rays. Energy of the gamma rays and intensities of the gamma rays derive from the elements (nuclei) that emit the gamma rays.

<Detection Depth Range Based on Thermal Neutrons and Fast Neutrons>

Out of neutrons included in a neutron beam from the neutron source 3, the thermal neutrons are captured by elements, but the fast neutrons are less likely to be captured by elements. Accordingly, at a high possibility, the thermal neutrons made incident on the inspection target 1 react with the target components that is in the inspection target 1 and that is in a range close to the surface $1a$. For example, this range is a range of several centimeters from the surface $1a$ when the inspection target 1 is a concrete structure. For this reason, the thermal neutrons are used to detect the target component in the range close to the surface $1a$.

Meanwhile, the fast neutrons made incident on the inspection target 1 hardly react with the target components in the range that is in the inspection target 1 and that is close to the surface $1a$, and the fast neutrons are repeatedly scattered in the inspection target 1 to become thermal neutrons. Thus, at a high possibility, the fast neutrons become thermal neutrons, and then react with the target components existing in a range deep from the surface $1a$ in the inspection target 1. For example, this range is a range of 10 cm to 30 cm from the surface $1a$ when the inspection target 1 is a concrete structure. For this reason, the fast neutrons are used to detect the target component in the range deep from the surface $1a$.

Therefore, by making neutron beams including both thermal neutrons and fast neutrons incident on the inspection target 1, it is possible to handle detection of the target components both in a range close to the surface $1a$ and in a range deep from the surface $1a$.

<Experiment>

A plurality of mortar specimens formed of mortar were prepared, and the experiment was performed. Respective concentrations (hereinafter, referred to as chloride ion concentrations) of chloride ions as the target component in these mortar specimens were set as 0.3 kg/m³, 0.5 kg/m³, 1 kg/m³, 3 kg/m³, and 5 kg/m³. Each of the mortar specimens has a cubic shape, and has each edge of 40 mm.

For each of the mortar specimens, a neutron beam was made incident on the mortar specimen by the neutron source 3, and an energy spectrum of the gamma rays thus generated in the mortar specimen was measured. For each of the mortar specimens, the experiment was performed under the same conditions. In other words, the conditions include the above-described neutron spectrum condition, distance condition, and orientation condition.

Figure 3:
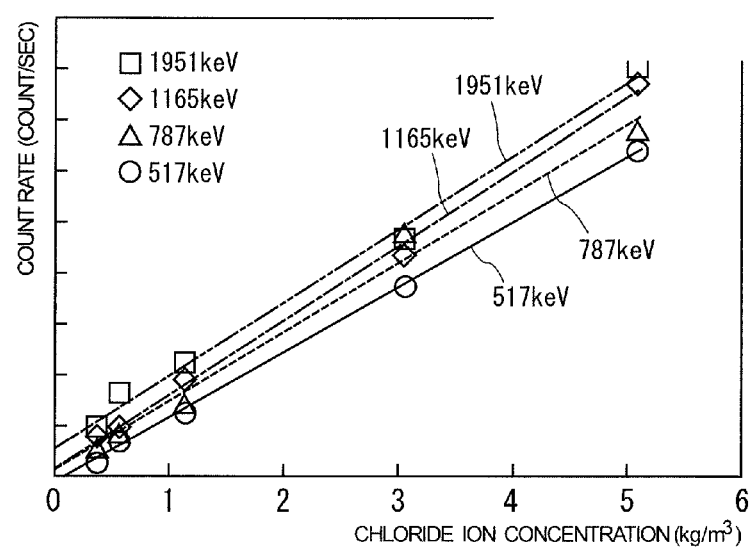
FIG. 3 illustrates a relation between a count rate $R_\gamma$ (count/second) of specific gamma rays detected by a gamma ray detector and a chloride ion concentration in an experiment.

FIG. 3 illustrates a relation between a chloride ion concentration and a count rate $R_\gamma$ (count/second) that is an intensity of the specific gamma rays detected by the gamma ray detector 5a in the experiment. FIG. 3 illustrates measurement results of specific gamma rays having energy values of 517 keV, 786 keV, 788 keV, 1165 keV, and 1951 keV. Note that 786 keV and 788 keV are values close to each other, and for this reason, in FIG. 3, the sum of detection intensities of the gamma rays of these two energy values is used as the count rate $R_\gamma$ of the specific gamma rays of one energy value 787 keV.

The count rate $R_\gamma$ indicates a total gamma-ray dose (gamma ray intensity) calculated from the number of times of detection of the gamma ray measured in unit time for each energy value. This total gamma-ray dose is a total dose of gamma rays radiated by $^{35}Cl$ that has captured neutrons. Specifically, the count rate $R_\gamma$ (count/second) was determined by the following equation (1).

$$R_\gamma = [\{(A/t)/\varepsilon_\gamma\}/I_\gamma]/(I_p/50) \quad (1)$$

Here, A indicates the number of times of detection of the specific gamma ray for each energy.

The symbol $\varepsilon_\gamma$ indicates gamma ray detection efficiency (%/100), and is a value acquired in advance using a standard gamma ray source or the like. The gamma ray detection efficiency is a ratio of the number of times a gamma ray is detected by the gamma ray detector 5a to a quantity of gamma rays from a gamma ray source (a position from which the gamma rays are emitted), is inversely proportional to energy of a gamma ray, and is inversely proportional to a distance between the gamma ray source and the gamma ray detector 5a. In order to determine a depth of the target component, $\varepsilon_\gamma$ for each energy value is set in the gamma ray detection device 5 on the assumption that a distance between the gamma ray source in the inspection target 1 and the gamma ray detector 5a is a predetermined constant value (this $\varepsilon_\gamma$ is written also as $\varepsilon_{\gamma S}$ or $\varepsilon_{\gamma d}$; the same applies to the second embodiment and third embodiment). Based on $\varepsilon_\gamma$ corresponding to each of the types of the specific gamma rays, the gamma ray detector 5 determines, as a detection intensity of the specific gamma ray of the type, an integrated value of a count rate $R_\gamma$ over the above-described measurement time.

In the first embodiment, the gamma ray detection efficiency (i.e., the gamma ray detection efficiency used at the below-described step S2) concerning calculation of a ratio between detection intensities of a plurality of types of the specific gamma rays is a value in a state where anything other than air does not exists between the gamma ray source and the gamma ray detector 5a.

Meanwhile, the gamma ray detection efficiency (e.g., the gamma ray detection efficiency used in the case of determining the above-described concentration data or used at the below-described step S5) concerning determination of a concentration of the target component may be a value depending on a material of the inspection target 1 or the specimen.

The symbol $I_\gamma$ indicates an intensity ratio (%/100) of the specific gamma ray when $^{35}Cl$ captures neutrons. In other words, $I_\gamma$ is a ratio representing the number of times of detection of each type of the specific gamma ray deriving from $^{35}Cl$. For example, $I_\gamma$ represents the number of times of detection of each type of the specific gamma rays when $^{35}Cl$ captures 100 neutrons. In one example, when $^{35}Cl$ captures 100 neutrons, the number of the emitted specific gamma rays of 1165 keV and the number of the emitted specific gamma rays of 1951 keV are 26.82 and 19.05, respectively (accordingly, $I_\gamma=0.2682$ and $I_\gamma=0.1905$ are input).

The symbol t indicates the above-described measurement time (second).

The symbol $I_p$ is an average current (μA) of the proton beam incident on the target 3d at the time of measurement, and 50 indicates that the count rate $R_\gamma$ is normalized by 50 μA. This numerical value does not need to be 50, and may be 10 or 100. The count rate $R_\gamma$ indicates an intensity of gamma rays.

As understood from FIG. 3, for each value of a chloride ion concentration, a count rate $R_\gamma$ becomes higher as energy of the specific gamma ray becomes higher. This indicates that a transmissivity of a gamma ray becomes higher as energy of a gamma ray becomes higher. The transmissivity represents a ratio of gamma rays that are among gamma rays generated in the mortar specimen or the inspection target 1 and that can pass through the surface of the mortar specimen or the inspection target 1. In other words, when among the total amount of gamma rays generated at a position of a predetermined depth from the surface in the mortar specimen or the inspection target 1, a certain amount of gamma rays pass through the surface, a ratio of the certain amount to the total amount is the transmissivity (the same applies to the following).

As understood from FIG. 3, a detection intensity of each type of the specific gamma rays becomes higher as a chloride ion concentration in the mortar specimen becomes higher. In FIG. 3, a chloride ion concentration and a detection intensity of the specific gamma rays are in a substantially proportional relation. Accordingly, it can be said that an intensity ratio between a plurality of types of specific gamma rays does not depend on a concentration of the target component (chlorine).

Using a combination of a difference in transmissivity between a plurality of types of the specific gamma rays and a difference in intensity ratio between a plurality of types of the specific gamma rays enables a depth of the target component to be determined as described below.

From FIG. 3, it is understood that a chloride ion concentration can be evaluated even when a chloride ion concentration is as low as 0.3 kg/m³. Thus, by the concentration evaluation unit 13, it can be detected whether chloride ion of a concentration causing corrosion of a reinforcing steel bar exists or not, since a lower limit value of a chloride ion concentration causing corrosion of a reinforcing steel bar is a value ranging from approximately 1.2 to 2.5 kg/m³.

<Theoretical Calculation of Transmissivity>

Figure 4:
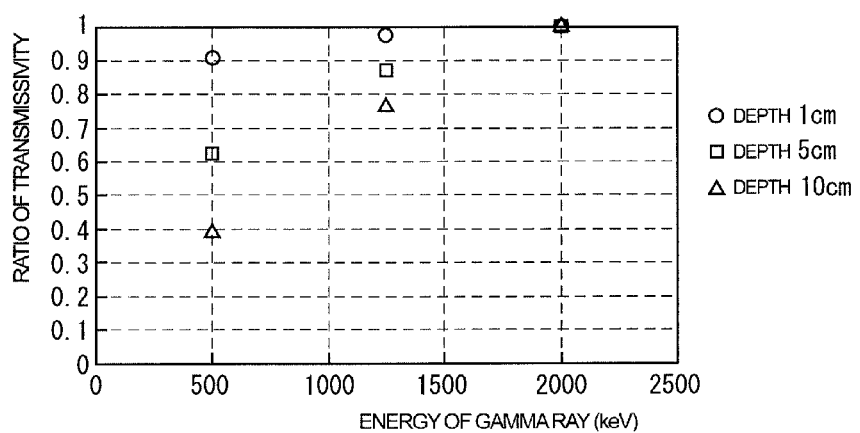
FIG. 4 represents, as ratios, theoretically calculated values of transmissivities of a plurality of types of gamma rays to a concrete.

FIG. 4 represents, as ratios, theoretical calculated values of transmissivities of a plurality of types of gamma rays to a concrete. In FIG. 4, the horizontal axis indicates energy of a gamma ray, and the vertical axis indicates a transmissivity representing a ratio of gamma rays that are among gamma rays generated in the concrete and that pass through the surface of the concrete. In other words, assuming that a transmissivity of a gamma ray having energy of 2000 keV is 1, a ratio of a transmissivity of each type of gamma rays to this transmissivity is indicated by the vertical axis. Energy of the respective types of gamma ray is 500 keV and 1250 keV.

In FIG. 4, the circle marks are calculated values for gamma rays generated at a depth of 1 cm from the surface of the concrete, the square marks are calculated values for gamma rays generated at a depth of 5 cm from the surface of the concrete, and the triangle marks are calculated values for gamma rays generated at a depth of 10 cm from the surface of concrete. As understood from FIG. 4, for each depth, a transmissivity becomes higher as energy of a gamma ray becomes higher.

<Detection Principle>

Figure 5:
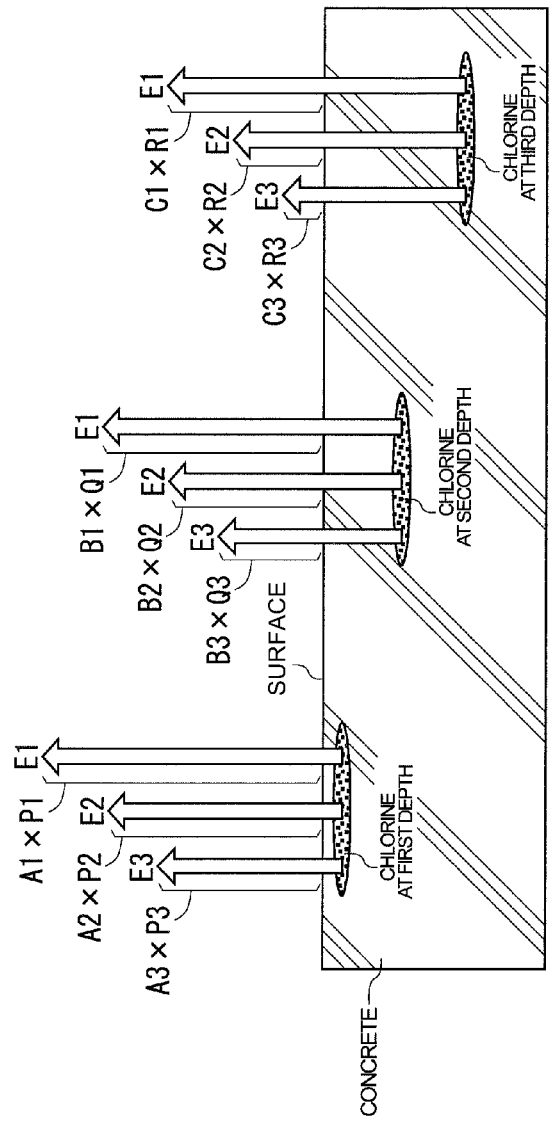
FIG. 5 is a schematic diagram illustrating a principle of depth detection of a target component according to the first embodiment.

FIG. 5 is a schematic view for illustrating the principle of depth detection of the target component according to the first embodiment. FIG. 5 illustrates the case where a neutron beam is made incident on a surface of a concrete as the inspection target 1, the neutrons react with chlorine in the concrete, and the specific gamma rays are generated.

As illustrated in FIG. 5, it is assumed that chlorine exists at a position whose depth from the surface is a first depth, a second depth, or a third depth in the concrete. It is assumed that when chlorine exists at the first depth, neutrons incident on the surface of the concrete react with the chlorine in the concrete, and thereby, a plurality of types of the specific gamma rays having energy E1, E2 and E3 are generated and emitted from the surface. Also in each of the cases where chlorine exists at the second depth and at the third depth, a plurality of types of the specific gamma rays having energy E1, E2 and E3 are similarly generated and emitted from the surface.

In FIG. 5, when chlorine exists at the first depth, the specific gamma rays of energy E1, E2, and E3 are generated at the first depth at intensities A1, A2, and A3, respectively, pass through the surface at transmissivities P1, P2, and P3, respectively, and are detected at intensities A1×P1, A2×P2, and A3×P3, respectively.

Similarly, when chlorine exists at the second depth, the specific gamma rays of energy E1, E2, and E3 are generated at the second depth at intensities B1, B2, and B3, respectively, pass through the surface at transmissivities Q1, Q2, and Q3, respectively, and are detected at intensities B1×Q1, B2×Q2, and B3×Q3, respectively.

Similarly, when chlorine exists at the third depth, the specific gamma rays of energy E1, E2, and E3 are generated at the third depth at intensities C1, C2, and C3, respectively, pass through the surface at transmissivities R1, R2, and R3, respectively, and are detected at intensities C1×R1, C2×R2, and C3×R3, respectively.

For the case of the first depth, a ratio between detection intensities of a plurality of types of the specific gamma rays that have passed through the surface is determined. For example, a ratio (A1×P1)/(A3×P3) of the detection intensity A1×P1 to the detection intensity A3×P3 is determined. This ratio does not depend on a chlorine concentration at the first depth. This is because A1 and A3 is each proportional to a chlorine concentration at the first depth, and accordingly, changes of A1 and A3 caused by a chlorine concentration cancel each other in A1/A3. Further, A1/A3 does not depend on the first depth. This is because an intensity of a neutron beam (thermal neutrons) reaching a certain depth (e.g., the first depth) is proportional to a depth, an intensity of gamma rays generated at the depth is proportional to an intensity of the neutron beam (thermal neutrons) that has reaches the depth, and accordingly, changes of A1 and A3 caused by a depth cancel each other in A1/A3. Thus, in the ratio (A1×P1)/(A3×P3), A1/A3 does not change depending on a concentration and an existence depth of chlorine, and is a value deriving from the target component. Meanwhile, transmissivities P1 and P3 are not proportional to the first depth, but are values that correspond to the first depth. Accordingly, an intensity ratio (A1×P1)/(A3×P3) is a value corresponding to the first depth.

Also in the case of the second depth, similarly, a ratio (B1×Q1)/(B3×Q3) of detection intensities is a value corresponding to the second depth. Also in the case of the third depth, a ratio of detection intensities (C1×R1)/(C3×R3) is a value corresponding to the third depth.

Accordingly, the above-described depth data representing a relation between such a ratio and a depth at which the target component (chlorine in this example) exists are acquired in advance, and based on the depth data and a ratio between detection intensities measured at the time of inspection, a depth at which the target component exists can be determined.

In the case where chlorine exists over a range from the surface to the third depth, a depth acquired by the above-described depth detection unit 11 is a rough value (e.g., an average depth) of a depth at which chlorine exists. Even in this case, from a depth output by the depth detection unit 11, a rough value of a depth at which the chlorine exists can be grasped. For example, when a depth output from the depth detection unit 11 is close to a position of a reinforcing steel bar in a concrete structure as the inspection target 1, it can be determined that the reinforcing steel bar may be corroded by chlorine (chloride ions). For the same inspection target 1, repeatedly acquiring a depth of chlorine at predetermined inspection date intervals (e.g., monthly or yearly) enables a change in chlorine permeation depth in the inspection target 1 to be grasped.

(Nondestructive Inspection Method)

Figure 6:
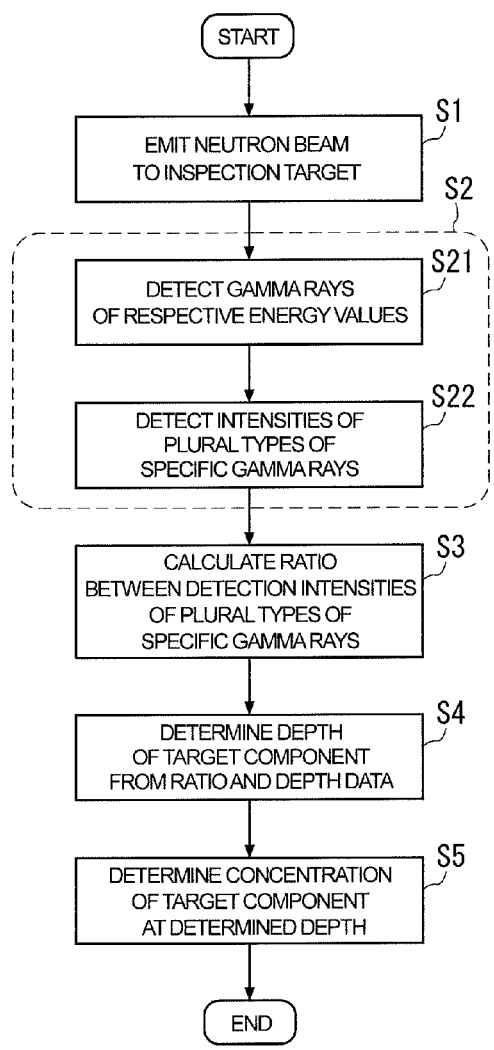
FIG. 6 is a flowchart illustrating a nondestructive inspection method according to the first embodiment.

FIG. 6 is a flowchart illustrating a nondestructive inspection method according to the first embodiment. The method may be performed using the above-described nondestructive inspection apparatus 10. The method includes steps S1 to S5.

At the step S1, the neutron source 3 emits a neutron beam to the surface 1a of the inspection target 1. Thereby, the neutron beam incident on the inspection target 1 reacts with the target component in the inspection target 1, and a plurality of types of the specific gamma rays deriving from the target component are generated.

At the step S2, the gamma ray detection device 5 detects, as detection intensities, intensities of a plurality of the types of the specific gamma rays generated at the step S1. The step S2 includes steps S21 and S22. At the step S21, the gamma ray detector 5a detects gamma rays of each energy values. At the step S22, the intensity detection unit 5b generates an energy spectrum of gamma rays, based on the detection data (a pulse height corresponding to energy of each detected gamma ray) acquired at the step S21, and detects, as a detection intensity, an intensity of each type of the specific gamma rays, based on the acquired energy spectrum, in accordance with the above-described equation (1). A gamma ray detection efficiency $\varepsilon_\gamma$ used at the step S2 is $\varepsilon_{\gamma S}$ described above.

At the step S3, based on a result of the detection at the step S2, an index value indicating a depth at which the target component exists is generated. In other words, the ratio calculation unit 7 calculates, as the index value, a ratio between the detection intensities of a plurality of types of the specific gamma rays detected at the step S2. In an embodied example, this ratio is a ratio of the detection intensity of the above-described second specific gamma rays to the detection intensity of the above-described first specific gamma rays.

At the step S4, based on the ratio calculated at the step S3 and the depth data in the depth data storage unit $9a$, the depth detection unit 11 determines a depth at which the target component exists.

At the step S5, based on the depth determined at the step S4, the concentration data concerning the determined depth and stored in the concentration data storage unit $9b$, and a detection intensity of the selection gamma rays, the concentration evaluation unit 13 determines a concentration of the target component at the determined depth.

In the case of using the concentration data acquired for each depth using the above-described equation (A), the step S5 is performed as follows. Based on the depth determined at the step S4, the concentration data concerning the determined depth and stored in the concentration data storage unit $9b$, and the detection intensity of the selection gamma rays, the concentration evaluation unit 13 determines a concentration of the target component at the determined depth. In this case, the gamma ray detection device 5 (the intensity detection unit $5b$) determines the number A of times of detection of the selection gamma ray, based on the energy spectrum of the gamma rays acquired at the above-described step S2, and detects a detection intensity of the selection gamma rays, based on the number A of times of detection and the above-described equation (A). This detection intensity is input to the concentration evaluation unit 13, and is used at the step S5 by the concentration evaluation unit 13. The detection intensity of the selection gamma rays used at this time may be newly extracted and acquired from the energy spectrum of the gamma rays acquired at the above-described step S2.

Meanwhile, when the concentration data for each depth are acquired using a gamma ray detection efficiency $\varepsilon_\gamma$ corresponding to the depth, the step S5 is performed as follows.

First, assuming that a gamma ray detection efficiency $\varepsilon_\gamma$ used at the step S2 is $\varepsilon_{\gamma S}$, and a gamma ray detection efficiency $\varepsilon_\gamma$ corresponding to the depth determined at the step S4 is $\varepsilon_{\gamma d}$, the intensity detection unit $5b$ detects a detection intensity of the selection gamma rays, based on the equation (1) in which $\varepsilon_{\gamma S}$ is replaced with $\varepsilon_{\gamma d}$, and based on the number A of times of detection of the selection gamma ray (e.g., already acquired or newly selected and acquired by the intensity detection unit $5b$, based on the energy spectrum of gamma rays acquired at the above-described step S2). In this case, as illustrated in FIG. 1, the detection efficiency storage unit 8 stores detection efficiency data representing a gamma ray detection efficiency $\varepsilon_\gamma$ corresponding to each depth in the inspection target 1 (i.e., a gamma ray detection efficiency $\varepsilon_\gamma$ used for acquiring concentration data for each depth and corresponding to each of these depths), and the intensity detection unit $5b$ specifies $\varepsilon_{\gamma d}$ described above, based on the detection efficiency data in the detection efficiency storage unit 8 and the depth (input from the depth detection unit 11) determined at the step S4, and uses the equation (1) in which $\varepsilon_{\gamma S}$ is replaced with $\varepsilon_{\gamma d}$ as described above.

Next, based on the detection intensity detected by the intensity detection unit $5b$, the depth determined at the step S4, and the concentration data concerning the determined depth and stored in the concentration data storage unit $9b$, the concentration evaluation unit 13 determines a concentration of the target component at the determined depth.

Advantageous Effects of First Embodiment

Intensities of a plurality of types of the specific gamma rays generated by reaction between the target component and neutrons incident on the above-described inspection target 1 are detected. As described above, a ratio between the detection intensities of a plurality of the specific gamma rays is a value corresponding to a depth at which the target component exists. In other words, this ratio indicates the depth at which the target component exists. For this reason, acquiring such a ratio enables detection of a depth at which the target component exists. Thus, a depth of the target component in the inspection target 1 can be detected non-destructively. For example, without extracting a core from a concrete structure as the inspection target 1, it is possible to detect a depth of a position of the target component existing in the inspection target 1, and to evaluate a concentration of the target component at the depth.

A gamma ray detection efficiency ($F_\gamma$ in the calculation equation (1) of the above-described count rate $R_\gamma$) at a depth in a concrete in which the target component exists is acquired in advance by an experiment (i.e., detection efficiency data are acquired in advance for acquisition of concentration data, as described above), and thereby, it can be also detected what amount of chlorine exists at the earlier-determined depth of a position of the target component.

For example, 1 kg/m$^3$ stated in the concrete specifications for concrete structures as a chloride ion concentration (marginal concentration) at which a steel member inside a concrete starts to corrode is set as a lower limit, or a concentration smaller than 1 kg/m$^3$ is set as a lower limit, and for a range from the lower limit to an assumed high concentration (e.g., 10 kg/m$^3$), the above-described concentration date are acquired (i.e., a calibration curve is drawn), and thereby, a concentration can be evaluated by comparing to each other data acquired at the time of actual measurement and the calibration curve (the concentration data). A chloride ion concentration at which a steel member inside a concrete starts to corrode varies depending on a type of concrete and a ratio of water and cement, and takes a value in a range from 1.2 to 2.5 kg/m$^3$.

In the first embodiment, the neutron source 3 may be configured such that an angle made by a direction in which the proton beam is incident on the target $3d$ and the direction of the neutron beam emission port in the neutron source 3 is 90 degrees. The neutron source 3 of this configuration emits, to the inspection target 1, a neutron beam in which among fast neutrons and thermal neutrons, a fast neutron component is greatly reduced such that the neutron beam is constituted mainly by the thermal neutrons. Thereby, a depth of the target component in an area near the surface $1a$ of the inspection target 1 can be detected accurately.

Meanwhile, in the first embodiment, when the below-described moderator $3g$ is not provided, or when the moderator $3g$ is provided, but a thermal neutron shielding material is installed on the surface $1a$ of the inspection target 1, and a neutron beam is made incident on the inspection target 1 via the thermal neutron shielding material, the neutron source 3 can irradiate the inspection target 1 with substantially only fast neutrons among thermal neutrons and fast neutrons. Thereby, a depth of the target component in an area deep from the surface $1a$ of the inspection target 1 can be detected accurately.

Second Embodiment

Figure 7:
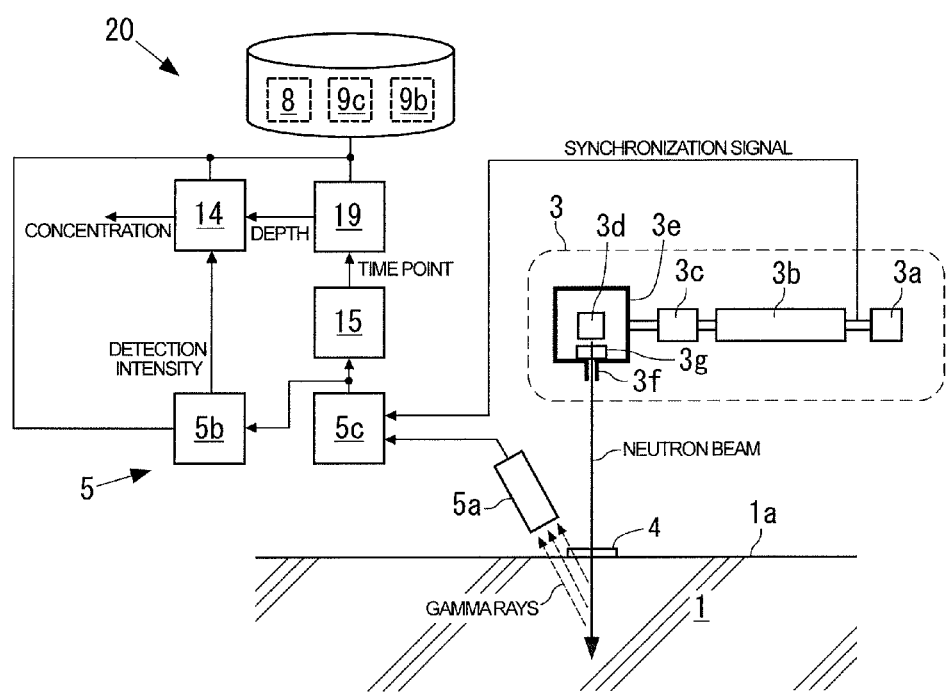
FIG. 7 illustrates a configuration of a nondestructive inspection apparatus according to a second embodiment of the present invention.

FIG. 7 illustrates a configuration of a nondestructive inspection apparatus 20 according to a second embodiment of the present invention. The configuration of the nondestructive inspection apparatus 20 according to the second embodiment differs in the below-described matters from the configuration of the nondestructive inspection apparatus 10 according to the first embodiment. Concerning the second embodiment, the matters that are not described below may be the same as those in the case of the first embodiment. In an embodied example of the second embodiment, the inspection target 1 is a concrete structure, and a target component is chlorine, but the inspection target 1 and the target component are not limited to this combination.

The nondestructive inspection apparatus 20 according to the second embodiment includes a neutron source 3, a gamma ray detection device 5, a time-point specifying unit 15, a depth data storage unit $9c$, a depth detection unit 19, and a concentration data storage unit $9b$, and a concentration evaluation unit 14.

Figure 8A:
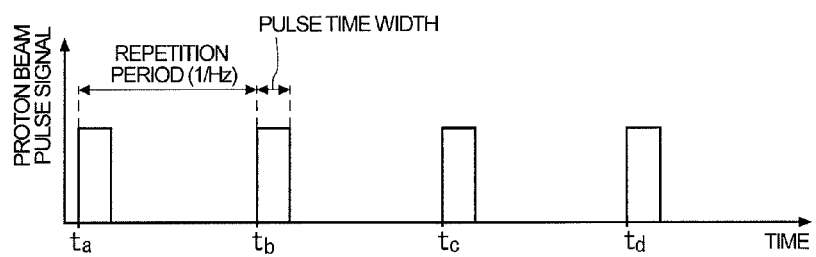
FIG. 8A illustrates a proton beam pulse signal with respect to time.

In the second embodiment, the neutron source 3 emits a pulse neutron beam. Duration of a pulse of a proton beam for the pulse neutron emission is approximately 0.1 milliseconds or is shorter than 0.1 milliseconds, for example, but is not limited to this as long as detection of a depth of the target component is not hindered. Similarly, a repetition frequency of the proton beam pulse is approximately 100 Hz, for example, but is not limited to this as long as detection of a depth of the target component is not hindered. FIG. 8A is a schematic diagram for illustrating a pulse time width and a repetition period (an inverse number of the repetition frequency) of the proton beam in the neutron source 3. In FIG. 8A, the horizontal axis represents time, the vertical axis represents magnitude of a proton beam pulse signal (the synchronization signal), and the repetition period is equal to the repetition period of the proton beam.

A pulse neutron beam is emitted under a distance condition. The distance condition is a condition that a distance between a surface $1a$ of an inspection target 1 (a specimen in the case of acquiring the below-described depth data) and an emission position of a pulse neutron beam in the neutron source 3 is a set distance. For example, this emission position may be a surface included in the target $3d$ and on a side of the inspection target 1. When the below-described moderator $3g$ is provided, the emission position may be a surface included in the moderator $3g$ and on a side of the inspection target 1.

The neutron source 3 further includes the moderator $3g$ through which neutrons generated in the target $3d$ pass. The moderator $3g$ is formed of a material (e.g., polyethylene) that decelerates fast neutrons passing therethrough to become thermal neutrons. Accordingly, neutrons generated in the target $3d$ pass through the moderator $3g$, thereby partially becomes thermal neutrons, and are then incident on the inspection target 1. Thus, the neutron source 3 can make thermal neutrons and fast neutrons incident on the inspection target 1.

A pulse neutron beam from the neutron source 3 is made incident on the inspection target 1, and reacts with the target component in the inspection target 1. Thereby, gamma rays (specific gamma rays) deriving from the target component are generated.

The gamma ray detector 5 detects the specific gamma rays generated by a pulse neutron beam incident on the inspection target 1. More specifically, the gamma ray detection device 5 detects an energy spectrum of gamma rays at each time point at and after a time point (i.e., a neutron generation time point as a reference time point) when the neutron source 3 makes a pulse proton beam incident on the target $3d$, and the gamma ray detection device 5 generates time-difference-to-spectrum data in which each time point (i.e., a time difference from the reference time point) with respect to the reference time is associated with the energy spectrum of the gamma rays detected at the time point concerned. The gamma ray detection device 5 includes a gamma ray detector $5a$, a data acquisition unit $5c$, and an intensity detection unit $5b$.

The gamma ray detector $5a$ detects, at each time point, an intensity of gamma rays for each energy (each wavelength) of gamma rays from the inspection target 1. In other words, the gamma ray detector $5a$ detects an energy spectrum of the gamma rays at each time point, and for each time point, outputs the energy spectrum to the data acquisition unit $5c$.

The data acquisition unit $5c$ generates the above-described time-difference-to-spectrum data representing an energy spectrum at each time point, based on an energy spectrum input from the gamma ray detector $5a$ at each time point. The energy spectrum at each time point indicates the number of times of detection of a gamma ray at each energy, concerning gamma rays detected at the time point concerned. In the second embodiment, each time point of detecting the energy spectrum represents a time difference between a neutron generation time point (the reference time point) and a gamma ray detection time point. The gamma ray detection time point may be a time point when the gamma ray detector $5a$ detects each gamma ray corresponding to the energy spectrum concerned.

Figure 9:
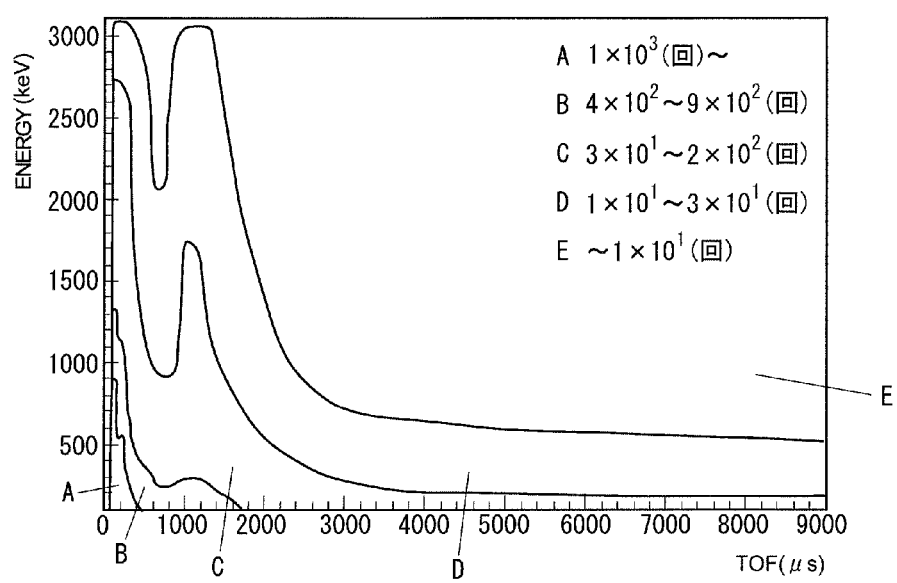
FIG. 9 illustrates an outline of an example of time-difference-to-spectrum data.

FIG. 9 illustrates an outline of an embodied example of the time-difference-to-spectrum data generated by the data acquisition unit $5c$. In FIG. 9, the horizontal axis indicates TOF (time of flight) that is a time difference between a neutron generation time point and a gamma ray detection time point, and the vertical axis indicates energy of a detected gamma ray. In FIG. 9, A indicates a region where the number of times a gamma ray having the corresponding energy is detected at the corresponding time point is approximately equal to or larger than $1\times10^3$, B indicates a region where the number of times a gamma ray having the corresponding energy is detected at the corresponding time point is approximately equal to or larger than $4\times10^2$ and equal to or smaller than $9\times10^2$, C indicates a region where the number of times a gamma ray having the corresponding energy is detected at the corresponding time point is approximately equal to or larger than $3\times10^1$ and equal to or smaller than $2\times10^2$, D indicates a region where the number of times a gamma ray having the corresponding energy is detected at the corresponding time point is approximately equal to or larger than $1\times10^1$ and equal to or smaller than $3\times10^1$, and E indicates a region where the number of times a gamma ray having the corresponding energy is detected at the corresponding time point is approximately equal to or smaller than $1\times10^1$.

The data acquisition unit $5c$ receives, from the neutron source 3, a synchronization signal indicating a proton beam incident time (neutron generation time), and generates the above-described time-difference-to-spectrum data, based on the synchronization signal. For example, the data acquisition unit $5c$ measures time, assuming that a time point of receiving the synchronization signal is the origin of time, and generates the time-difference-to-spectrum data in which each time point with respect to the origin is associated with an energy spectrum detected by the gamma ray detector 5a at the time point concerned.

The intensity detection unit 5b acquires a detection intensity of the specific gamma rays, based on the time-difference-to-spectrum data acquired or generated by the data acquisition unit 5c. Here, the specific gamma ray is a selection gamma ray concerning the below-described concentration data, and the detection intensity is a value proportional to the number of times the specific gamma ray is detected over the predetermined measurement time described above in the first embodiment.

The time-point specifying unit 15 specifies a time point when the specific gamma ray is detected, based on the time-difference-to-spectrum data acquired or generated by the gamma ray detection device 5 (data acquisition unit 5c). For example, based on the time-difference-to-spectrum data, the time specifying unit 15 specifies a time point of detected energy of the specific gamma ray in the energy spectrums at respective time points detected by the gamma ray detector 5a. In one example, the time-point specifying unit 15 extracts, from the above-described time-difference-to-spectrum data, data indicating the number of times of detection of the specific gamma ray at each time point, and specifies, based on the extracted data, a time point (i.e., a specific time point) when the specific gamma ray is detected, as a time point when energy of the specific gamma ray is detected.

When incidence of a pulse neutron beam on the inspection target 1 causes a plurality of types of the specific gamma rays to be radiated from the target component, the time specifying unit 15 may specify a time point when the pre-designated type of specific gamma ray (hereinafter, referred to also as a designated gamma ray) is detected.

The depth data storage unit 9c stores the depth data representing a relation between a depth at which the target component exists in the inspection target 1 and a specific time point (a time point with respect to the reference time point) when the specific gamma ray (designated gamma ray) deriving from the target component is detected in the case where a pulse neutron beam is made incident on the inspection target 1. The depth data may be acquired by an experiment, for example.

In this experiment, a plurality of specimens formed of the same material as the inspection target 1 are prepared. A depth at which the target component exists in each of a plurality of the specimens differs between these specimens. For each specimen, the above-described neutron source 3 makes a pulse neutron beam incident on a surface of the specimen, and the time-point specifying unit 15 specifies a detection time point of energy of the specific gamma ray (designated gamma ray), from energy spectrums of gamma rays at respective time points detected by the gamma ray detector 5a. The depth of the target component in one specimen and the detection time point (specific time point) specified for this specimen are assumed to constitute one set of data, and based on a plurality of sets of data acquired for a plurality of the specimens, the above-described depth data are generated. The thus-generated depth data are stored in advance in the depth data storage unit 9c.

The above-described experiment for acquiring the depth data and actual inspection (the below-described step S101) of the inspection target 1 is performed under the above-described distance condition. Further, the above-described experiment for acquiring the depth data and actual inspection (the below-described step S101) of the inspection target 1 may be performed under the above-described neutron spectrum condition and orientation condition.

The depth detection unit 19 determines a depth at which the target component exists, based on the depth data stored in the depth data storage unit 9c and a time point specified by the time-point specifying unit 15. At this time, the depth detection unit 19 may apply this time point to the depth data, thereby determining a depth at which the target component exists. The depth detection unit 19 outputs the determined depth. The output depth may be input to the concentration evaluation unit 14, be stored in an appropriate storage medium, be displayed on a display, or be printed on a paper sheet.

Figure 8B:
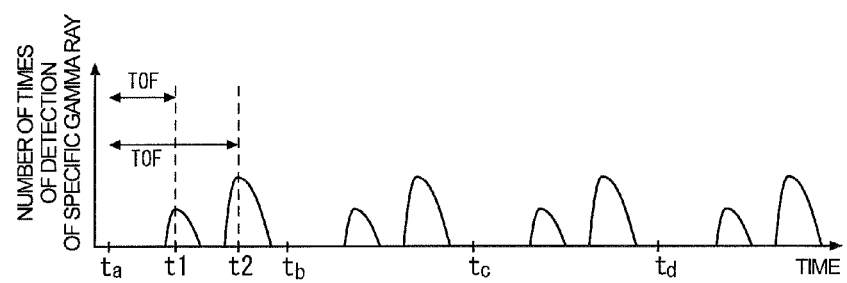
FIG. 8B illustrates the number of times of detection of a specific gamma ray with respect to time.

For example, when the moderator 3g is provided as described above, and thereby, the neutron source 3 makes both fast neutrons and thermal neutrons incident on the surface 1a of the inspection target 1, one or both of depth data for fast neutrons and depth data for thermal neutrons are acquired in advance as described above. Regarding this, the following description is made with reference to FIG. 8B. In FIG. 8B, the horizontal axis indicates time, and the vertical axis indicates the number of times of detection of the specific gamma ray. Time points $t_a$, $t_b$, $t_c$, and $t_d$ in FIG. 8B correspond to time points $t_a$, $t_b$, $t_c$, and $t_d$ in FIG. 8A, respectively.

A distance between an emission position of the neutron source 3 and the surface 1a of the inspection target 1 and a pulse width and a repetition frequency of a proton beam are set in advance by a simulation or an experiment such that when data representing the number of times of detection of the specific gamma ray at each time point are extracted from the above-described time-difference-to-spectrum data as described above, in the extracted data (e.g., data in FIG. 8B), concerning a time point (specific time point) of detecting the specific gamma ray, a specific time point (e.g., the time point t1 in FIG. 8B) occurring due to fast neutrons emitted to the surface 1a of the inspection target 1 by the neutron source 3 is shifted distinguishably from a specific time point (e.g., the time point t2 in FIG. 8B) occurring due to thermal neutrons emitted to the surface 1a of the inspection target 1 by the neutron source 3. This is enabled by the matter that the fast neutrons differ in a moving speed from the thermal neutrons. In other words, gamma rays caused by the emitted fast neutrons are detected at earlier time points, and gamma rays caused by the emitted thermal neutrons are detected at later time points. When a pulse width of a proton beam is large in FIG. 8A, a width (time width) of a waveform representing the number of times of detection in FIG. 8B is widened. When a distance between an emission position of the neutron source 3 and the surface 1a of the inspection target 1 is short, the time point t1 and the time point t2 in FIG. 8B become close to each other. In consideration of these, the distance, the pulse width, and the repetition frequency are set in advance.

In the present embodiment, the specific time point is a specific time point within a time range in which the number of times of detection of the specific gamma ray occurs, and for example, may be a time point when the number of times of detection becomes a peak, or may be a time point when the number of times of detection starts to occur.

When both the depth data for fast neutrons and the depth data for thermal neutrons are acquired, for example, the depth detection unit 19 extracts, from the above-described time-difference-to-spectrum data, data representing the number of times the specific gamma ray is detected at each time point, and determines a depth at which the target component exists, based on the depth data for fast neutrons and the earlier specific time point (t1) of the two specific time points (e.g., t1 and t2 in FIG. 8B) of the number of times of detection of the specific gamma ray in the extracted data, or based on the depth data for thermal neutrons and the later specific time point (t2) of the two specific time points.

In the above description, the neutron source 3 is configured so as to irradiate the inspection target 1 with thermal neutrons and fast neutrons. In this case, it is possible to detect the target component existing in a range near the surface 1a and in a range deep from the surface 1a in the inspection target 1.

Meanwhile, when the moderator 3g is omitted, or when a thermal neutron shielding material 4 (FIG. 7) is installed on the surface 1a of the inspection target 1 in the configuration in which the moderator 3g is provided, the neutron source 3 irradiates the inspection target 1 with substantially only fast neutrons among thermal neutrons and fast neutrons. In this case, it is possible to detect a depth of the target component existing in a range deep from the surface 1a in the inspection target 1. In this case, the depth data for thermal neutrons do not need to be acquired.

The concentration data storage unit 9b in the second embodiment is the same as the concentration data storage unit 9b in the first embodiment. In other words, the concentration data storage unit 9b stores the concentration data representing a relation between a detection intensity of the selection gamma ray and a concentration of the target component. Here, the selection gamma ray may be the above-described designated gamma ray, or another type of the specific gamma ray.

Based on a depth determined by the depth detection unit 19, the concentration data stored in the concentration data storage unit 9b and corresponding to the depth concerned, and an input detection intensity of the selection gamma ray, the concentration evaluation unit 14 determines a concentration of the target component at the depth concerned. The concentration evaluation unit 14 outputs the determined concentration. The output concentration may be stored in an appropriate storage medium, be displayed on a display, or be printed on a paper sheet.

(Nondestructive Inspection Method)

Figure 10:
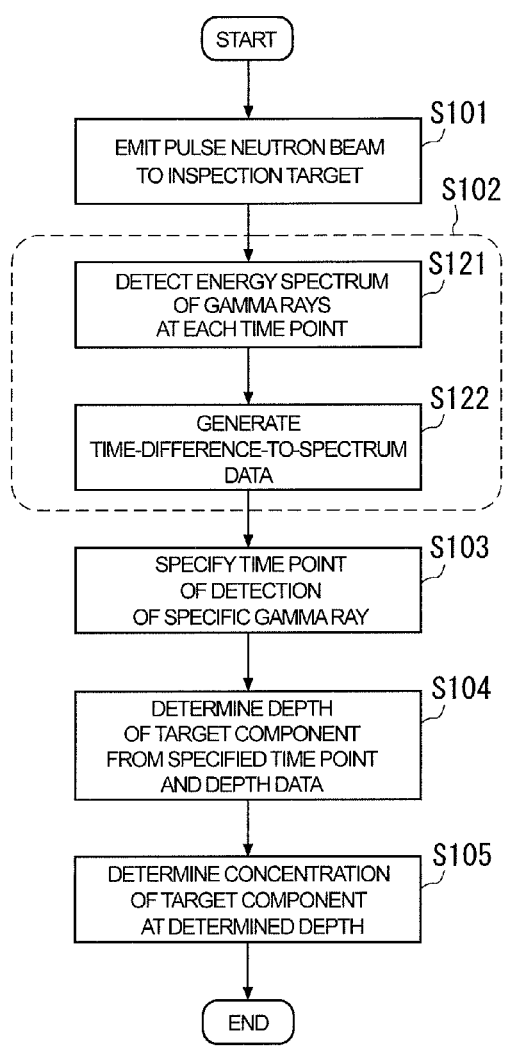
FIG. 10 is a flowchart illustrating a nondestructive inspection method according to the second embodiment.

FIG. 10 is a flowchart illustrating a nondestructive inspection method according to the second embodiment. This method may be performed using the above-described nondestructive inspection apparatus 20. The method includes steps S101 to S105.

At the step S101, the neutron source 3 emits a pulse neutron beam to the surface 1a of the inspection target 1. Thereby, the pulse neutron beam that has been made incident on the inspection target 1 reacts with the target component in the inspection target 1, causing the specific gamma rays deriving from the target component to be generated.

At the step S102, the specific gamma rays that are among gamma rays generated at the step S101 and that derive from the target component in the inspection target are detected, and a time point when the specific gamma rays (designated gamma rays) are detected is specified. In the present embodiment, the step S102 may include steps S121 and S122. At the step S121, the gamma ray detector 5a detects an energy spectrum of the gamma rays at each time point. At the step S122, assuming that a time point when the above-described synchronization signal is received is the origin, time is measured, and meanwhile, time-difference-to-spectrum data in which the energy spectrum detected by the gamma ray detector 5a at each measurement time point is associated with the time point concerned are generated.

At the step S103, based on a result of the detection at the step S102, the time-point specifying unit 15 specifies a time point when the specific gamma ray (designated gamma ray) is detected at or after the time point when the pulse neutron beam is emitted at the step S101. At this time, based on the time-difference-to-spectrum data generated at the step S122, the time-point specifying unit 15 may specify a time point when the specific gamma ray is detected.

At the step S104, the depth detection unit 19 determines a depth at which the target component exists, based on the time point specified at the step S103 and the depth data in the depth data storage unit 9c.

At the step S105, based on the depth determined at the step S104, the concentration data that are relevant to the depth concerned and that are stored in the concentration data storage unit 9b, and a detection intensity of the selection gamma rays, the concentration evaluation unit 14 determines a concentration of the target component at the depth concerned.

When the concentration data acquired for each depth by using the above-described equation (A) are used, the step 105 is performed as follows.

First, based on the equation (A) and the number A of times of detection of the selection gamma ray, the intensity detection unit 5b determines a detection intensity of the selection gamma rays. The number A of times of detection used at this time is based on a detection result that concerns the selection gamma rays and that is acquired (e.g., at the step S102, or by being newly selected at the step S102) for the inspection target 1 by the neutron source 3 and the gamma ray detection device 5.

Next, based on the detection intensity of the selection gamma rays determined by the intensity detection unit 5b, the depth determined at the step S104, and the concentration data that are relevant to the depth concerned and that are stored in the concentration data storage unit 9b, the concentration evaluation unit 14 determines a concentration of the target component at the depth concerned.

Meanwhile, when the concentration data for each depth are acquired using a gamma ray detection efficiency $\varepsilon_\gamma$ corresponding to the depth concerned, the step S105 is performed as follows.

First, assuming that a gamma-ray detection efficiency $\varepsilon_\gamma$ corresponding to the depth determined at the step S104 is $\varepsilon_{\gamma d}$, the intensity detection unit 5b determines a detection intensity of the selection gamma rays, based on the above-described equation (1) and the number A of times of detection of the selection gamma ray. The number A of times of detection used at this time is based on a detection result that concerns the selection gamma rays and that is acquired (e.g., at the step S102, or by being newly selected at the step S102) for the inspection target 1 by the neutron source 3 and the gamma ray detection device 5. The same detection efficiency data as that in the first embodiment are stored in the detection efficiency storage unit 8 as illustrated in FIG. 7, and the intensity detection unit 5b specifies Era described above, based on the detection efficiency data in the detection efficiency storage unit 8 and the depth determined at the step S104, and uses the equation (1) as described above.

Next, based on the detection intensity of the selection gamma rays determined by the intensity detection unit 5b, the depth (the depth input from the depth detection unit 19) determined at the step S104, and the concentration data that are relevant to the depth concerned and that are stored in the concentration data storage unit 9b, the concentration evaluation unit 14 determines a concentration of the target component at the depth concerned.

Advantageous Effect of Second Embodiment

The specific gamma rays generated by reaction between the target component and neutrons incident on the inspection target 1 are detected, and a time point when the specific gamma ray is detected is specified. The specified time point indicates a depth at which the target component exists. Accordingly, determining such a time point enables detection of a depth at which the target component exists. Thus, a depth of the target component in the inspection target 1 can be detected nondestructively. For example, without extracting a core from a concrete structure as the inspection target 1, it is possible to detect a depth of a position of the target component existing in the inspection target 1, and to evaluate a concentration of the target component at this depth.

Third Embodiment

Principle of Third Embodiment

Figure 11A:
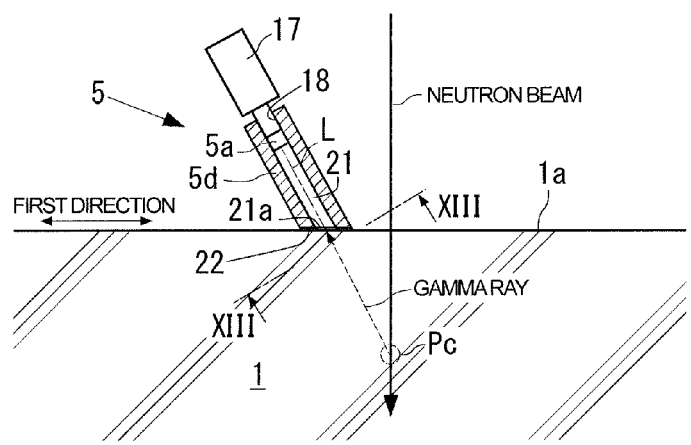
FIG. 11A illustrates a detection principle according to a third embodiment.

FIG. 11A illustrates the detection principle according to a third embodiment. In the third embodiment, the gamma ray detection device 5 collimates gamma rays to be detected. In other words, the gamma ray detection device 5 detects gamma rays that are among gamma rays generated at a specific depth in the inspection target 1 and that have traveled in a direction within a specific range. More specifically, a neutron beam whose cross-sectional size is reduced is made incident on the inspection target 1, and on the assumption that a position Pc (hereinafter, also referred simply as an intersection position Pc) is a position at which a reference straight line L of the gamma ray detector 5a intersects with a straight line path of the neutron beam, gamma rays that are among gamma rays generated at the intersection position Pc and that have traveled along the reference straight line L are selectively made incident on the gamma ray detector 5a, and the below-described gamma ray shielding portion 5d prevents the gamma rays traveling in other directions from being incident on the gamma ray detector 5a.

Thus, when the gamma ray detection device 5 detects the specific gamma rays deriving from the target component, it is understood that the target component exists at the intersection position Pc (depth). By changing a geometrical relation (a relation concerning a position and an orientation) between the reference straight line L and a neutron beam path, it can be inspected whether or not the target component exists at each intersection position Pc.

A neutron beam is made incident on the inspection target 1 in a state where a size of a cross section of the neutron beam is reduced so as to be equal to or smaller than an upper limit value. The upper limit value may be equal to or smaller than several tens of millimeters, and for example, is equal to or smaller than 50 millimeters or is equal to or smaller than 30 millimeters. A degree of size reduction of a neutron beam may be set in the neutron source 3, depending on a required resolution of the intersection position Pc. When a cross section of a neutron beam is large, the number of times of detection of a gamma ray increases, but a resolution of the intersection position Pc is lowered. When a cross section of a neutron beam is small, the number of times of detection of a gamma ray decreases, but a resolution of the intersection position Pc is raised. A cross-sectional shape of a neutron beam may be a circular shape or a shape similar to a circular shape, for example, but is not limited to these, and may be an elliptical shape, a rectangular shape, or the like.

Figure 11B:
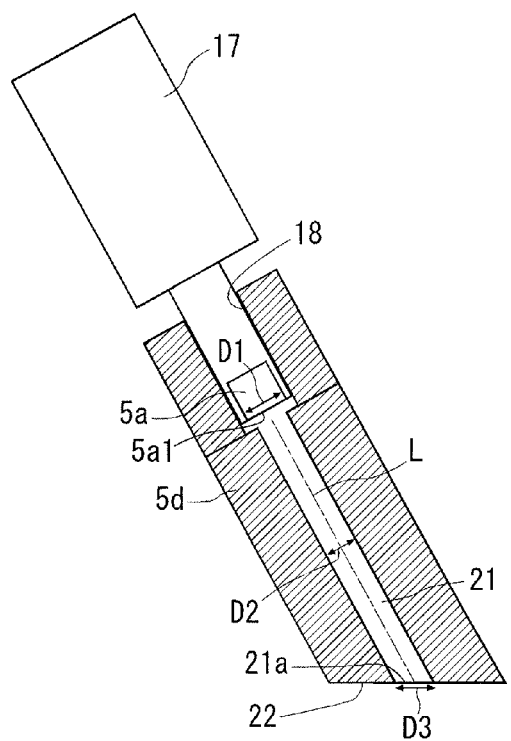
FIG. 11B is a partially enlarged view of FIG. 11A.

A degree of collimating gamma rays (an area of an opening 21a of the below-described gamma ray shielding portion 5d) is set depending on a degree of a spread of a range (intersection position Pc), with gamma rays from this range being to be detected. When an area of the opening 21a is large, the number of times of detection of a gamma ray increases, but a resolution of the intersection position Pc is lowered. When an area of the opening 21a is small, the number of times of detection of a gamma ray decreases, but a resolution of the intersection position Pc is raised. FIG. 11B is a partial enlarged view of FIG. 11A, and illustrates one example of shapes of the gamma ray detectors 5a and the gamma ray shielding portion 5d. As illustrated in FIG. 11B, the gamma ray detector 5a includes a detection surface 5a1, and detects gamma rays incident on the detection surface 5a1. An area D1 of the detection surface 5a1 is larger than a cross-sectional area D2 of a gamma ray passage hole 21 of the gamma ray shielding portion 5d, and is larger than an area D3 of the opening 21a. In other words, the gamma ray detector 5a and the gamma ray shielding portion 5d may be formed such that in viewing in the direction of the center line L of the gamma ray passage hole 21, the gamma ray passage hole 21 and the opening 21a are smaller than the detection surface 5a1 as illustrated in FIG. 11B, for example.

Configuration of Third Embodiment

Figure 12:
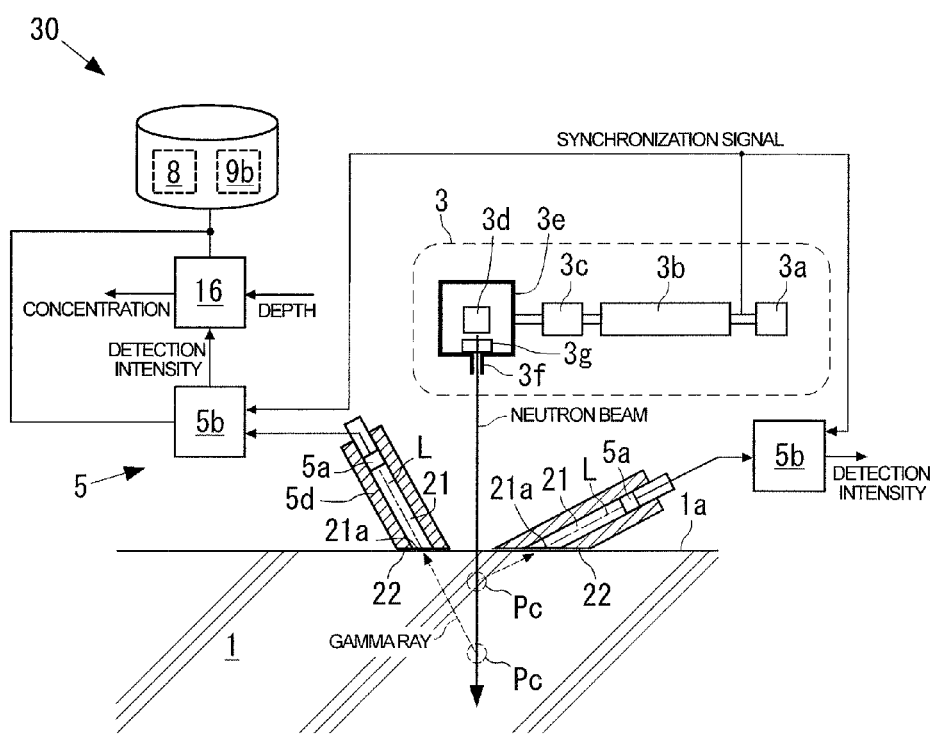
FIG. 12 illustrates a configuration of a nondestructive inspection apparatus according to a third embodiment of the present invention.

FIG. 12 illustrates a configuration of a nondestructive inspection apparatus 30 according to a third embodiment of the present invention. The nondestructive inspection apparatus 30 includes the gamma ray detection device 5 and the neutron source 3 that is described in the first embodiment or the second embodiment. In the third embodiment, the gamma ray detection device 5 includes the below-described configuration. In the third embodiment, concerning the gamma ray detection device 5, the matters that are not described below may be the same as those in the case of the first embodiment or the second embodiment described above.

In the third embodiment, the gamma ray detector 5 includes the gamma ray detector 5a, an intensity detection unit 5b, and the gamma ray shielding portion 5d.

The gamma ray detector 5a detects gamma rays for each energy of gamma rays generated in the inspection target 1 by the incident neutron beam, and inputs detection data thereof to the intensity detection unit 5b. The detection data may be a pulse height corresponding to energy of each detected gamma ray. The gamma ray detector 5a may be a germanium detector, for example, but is not limited to this.

The intensity detection unit 5b acquires an energy spectrum of the gamma rays, based on pulse heights input from the gamma ray detector 5a. Based on the energy spectrum, the intensity detection unit 5b determines, as a detection intensity, an intensity of the specific gamma rays. When a plurality of types of the specific gamma rays are emitted from the target component by a neutron beam incident on the inspection target 1, the intensity detection unit 5b determines, as a detection intensity, an intensity of a designated type of the specific gamma rays. The intensity detection unit 5b outputs the determined detection intensity of the specific gamma rays. The output detection intensity may be displayed on a display.

The gamma ray shielding portion 5d is formed of a material (e.g., lead, tungsten, tantalum, or iron) having a high ability of shielding against gamma rays, and thereby substantially prevents gamma rays from passing therethrough. The gamma ray shielding portion 5d forms the gamma ray passage hole 21. The gamma ray passage hole 21 includes the opening 21a through which gamma rays are allowed to enter. The gamma ray detector 5a is arranged at a position shifted from the opening 21a to a deep side in the gamma ray passage hole 21. The opening 21a and the gamma ray detector 5a are positioned on the reference straight line L. By such a gamma ray shielding portion 5d, the gamma ray detector 5a detects substantially only gamma rays entering along the reference straight line L from the opening 21a. The reference straight line L may be the center line of the gamma ray passage hole 21.

When the gamma ray detector 5a is the germanium detector 5a, a cooling device 17 (unillustrated in FIG. 12, but illustrated in FIG. 11A and FIG. 11B) that cools the germanium detector 5a is provided. The cooling device 17 may be provided outside the gamma ray shielding portion 5d. In this case, the cooling device 17 may cool the germanium detector 5a through a hole 18 provided in the gamma ray shielding portion 5d on a side opposite to the opening 21a.

The gamma ray shielding portion 5d includes a front end surface 22 on which the opening 21a is formed. The reference straight line L may extend obliquely relative to the front end surface 22. In other words, the front end surface 22 is formed such that the reference straight line L extends obliquely relative to the front end surface 22. With this configuration, by performing inspection in a state where the front end surface 22 faces the surface 1a of the inspection target 1 as illustrated in FIG. 12, gamma rays from positions other than positions on an extension line of the reference straight line L can be more reliably prevented from leading to the gamma ray detector 5a. As a result, a resolution of the intersection position Pc is improved. The front end surface 22 may be a plane, but is not limited to this.

Figure 13A:
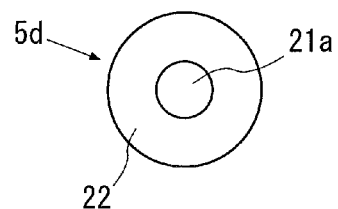
FIG. 13A is a view taken along the line XIII-XIII in FIG. 11A, illustrating a concrete example of a shape of a gamma ray shielding portion.
Figure 13B:
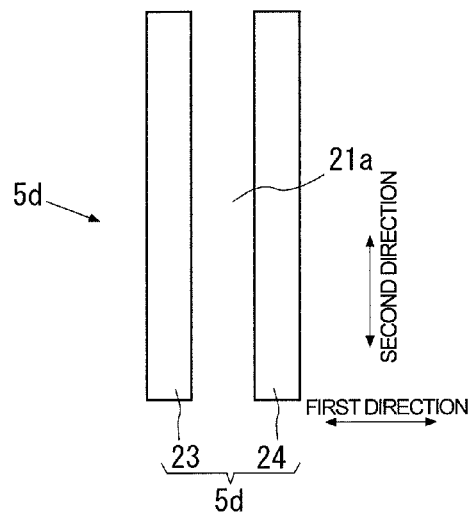
FIG. 13B is a view taken along the line XIII-XIII in FIG. 11A, illustrating another concrete example of a shape of the gamma ray shielding portion.

FIG. 13A and FIG. 13B illustrate concrete examples of a shape of the gamma ray shielding portion 5d. FIG. 13A and FIG. 13B are each a view taken along the line XIII-XIII in FIG. 11A, but illustrate the concrete examples different from each other.

In the case of FIG. 13A, the gamma ray shielding portion 5d is formed so as to surround an entire circumference of the gamma ray passage hole 21. In this case, the cross-sectional shape of the gamma ray passage hole 21 may be circular as illustrate in FIG. 13A, or may be another shape.

In the case of FIG. 13B, the gamma ray shielding portion 5d includes two shielding blocks 23 and 24 that are separated by a gap from each other and that are formed of the above-described material so as to substantially prevent gamma rays from passing therethrough. The gap is the gamma ray passage hole 21. The gap 21 extends along the reference straight line L. A size of the gap 21 in a first direction perpendicular to the reference straight line L is smaller than a size of the gap 21 in a second direction perpendicular to both the reference straight line L and the first direction. For example, a size of the gap 21 in the first direction is equal to or smaller than one half, one third, or one fifth of a size of the gap 21 in the second direction.

In the case of FIG. 13B, a size of the cross section of the neutron beam is set to be equal to or smaller than the above-described upper limit value in at least the first direction of the first and second directions.

Assuming that the gamma ray detector 5a, the intensity detection unit 5b, and the gamma ray shielding unit 5d associated with each other form one set, the gamma ray detection device 5 may include one set or a plurality of sets. In FIG. 12, two sets are illustrated. The gamma ray shielding units 5d associated with the respective gamma ray detectors 5a in FIG. 12 may each have the shape described based on FIG. 13A or FIG. 13B.

The concentration data storage unit 9b in the third embodiment is the same as the concentration data storage unit 9b in the first embodiment. In other words, the concentration data storage unit 9b stores concentration data representing a relation between a detection intensity of the selection gamma ray and a concentration of the target component.

Based on a depth determined as described later, the concentration data stored in the data storage unit 9b and associated with the determined depth, and an input detection intensity of the selection gamma ray, the concentration evaluation unit 16 determines a concentration of the target component at the determined depth. The concentration evaluation unit 16 outputs the determined concentration. The output concentration may be stored in an appropriate storage medium, be displayed on a display, or be printed on a paper sheet.

(Nondestructive Inspection Method)

Figure 14:
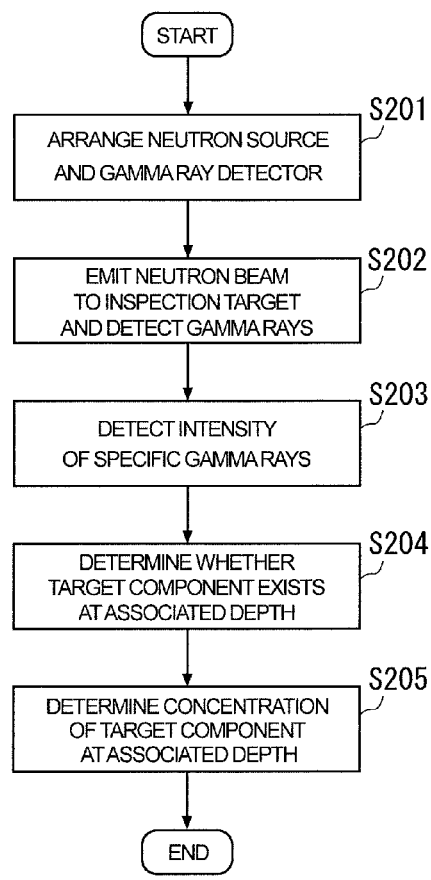
FIG. 14 is a flowchart illustrating a nondestructive inspection method according to the third embodiment.

FIG. 14 is a flowchart illustrating the non-destructive inspection method according to the third embodiment. This method may be performed using the above-described non-destructive inspection apparatus 30 described above. The method includes steps S201 to S205.

At the step S201, the neutron source 3 and the gamma ray detection device 5 are arranged such that a path of a neutron beam emitted from the neutron source 3 and an extension line of the reference straight line L of the gamma ray shielding portion 5d intersect with each other inside the inspection target 1. In this arrangement, the gamma ray shielding portion 5d and the gamma ray detector 5a may be arranged such that the front end surface 22 of the gamma ray shielding portion 5d faces the surface 1a of the inspection target 1 (e.g., the flat front end surface 22 is parallel to the flat surface 1a). In this case, further, the front end surface 22 may contact with the surface 1a, or a slight gap may be provided between the front end surface 22 and the surface 1a. The incident neutron beam does not need to be perpendicular to the surface 1a of the inspection target 1, and the neutron beam may be made obliquely incident on the surface 1a. Arrangement of the gamma ray detector 5a may be changed depending on an angle between the incident neutron beam and the surface 1a.

The step S202 is performed in a state of the arrangement made at the step S201. At the step S202, by the neutron source 3, a neutron beam is made incident on the surface 1a of the inspection target 1. At the step S202, the gamma ray detector 5a detects gamma rays of respective values of energy generated by the incidence of the neutron beam, and inputs the detection data to the intensity detector 5b. The neutron beam made incident on the surface 1a at the step S202 may be a pulse neutron beam as in the second embodiment, or a temporally continuous neutron beam.

At the step S203, based on the detection data (a pulse height corresponding to energy of each detected gamma ray) acquired at the step S202, the energy detection unit 5b acquires an energy spectrum of the gamma rays, and based on the energy spectrum, the energy detection unit 5b acquires, as a detection intensity, an intensity of the specific gamma rays (i.e., selection gamma rays) by the equation (A), for example. Further, at the step S203, the detection intensity is output from the intensity detection unit 5b.

At the step S204, based on the detection intensity of the specific gamma rays output at the step S203, it is determined whether or not the target component exists at a depth (hereinafter, also referred to as an associated depth) that is in the inspection target 1 and that is associated with the reference straight line L at the step S201. The associated depth is a depth of the intersection position Pc surrounded by the broken-line circle in FIG. 11A or FIG. 12. In other words, the associated depth is a depth of an intersection position between a path of the neutron beam emitted from the neutron source 3 and the extension line of the reference straight line L.

The intersection position Pc (associated depth) can be determined at the step S204, based on a geometrical relation among the inspection target 1 and the neutron source 3 and the gamma ray detection device 5 arranged at the step S201. For example, the geometrical relation is detected by using an appropriate sensor or measurement device, a result of this detection is input to an appropriate computing device, and the computing device determines the intersection position Pc. Alternatively, based on the result of this detection, a person may determine the intersection position Pc by calculation. The thus-determined intersection position Pc includes the associated depth and a position in directions along the surface 1a. An example of the geometrical relation may be a relation concerning a position and a direction among the path of the neutron beam, the reference straight line L, and the surface 1a of the inspection target 1.

The determination at the step S204 may be performed by a person. For example, when the detection intensity of the specific gamma rays output at the step S203 is displayed on a display, and the person looks at the displayed detection intensity, and determines that the target component exists at the associated depth, when the detection intensity is equal to or larger than a set lower limit value. The associated depth determined by the computing device as described above may be displayed on the display along with the detection intensity.

At the step S205, a concentration of the target component at the associated depth (intersection position Pc) determined at the step S204 is determined. In this case, based on the above-described concentration data, the associated depth, and the detection intensity determined at the step S203, the concentration evaluation unit 16 determines a concentration of the target component at the associated depth. The associated depth used at this time is determined at the step S204 as described above, and may be input to the concentration evaluation unit 16 and the intensity detection unit 5b by the above-described computing device or by a person operating an appropriate operation unit.

In the case of using the concentration data acquired for each depth by using the equation (A), the step 205 is performed as follows.

First, based on the above-mentioned equation (A) and the number A of times of detection of the selection gamma ray, the intensity detection unit 5b determines a detection intensity of the selection gamma rays. The number A of times of detection used at this time is based on a result of detection of the selection gamma rays acquired (at the step S202 or by being newly selected at the step S202, for example) for the inspection target 1 by the neutron source 3 and the gamma ray detection device 5 under the same conditions as the above-described conditions including the orientation condition when the concentration data are acquired.

Next, based on the detection intensity of the selection gamma rays determined by the intensity detection unit 5b, the associated depth determined at the step S204, and the concentration data for the associated depth stored in the concentration data storage unit 9b, the concentration evaluation unit 16 determines a concentration of the target component at the associated depth.

Such concentration evaluation may be performed by a person. For example, the detection intensity, the concentration data for each depth, and the associated depth may be displayed on a display, and a person may look at these pieces of the displayed data and determine a concentration of the target component at the associated depth.

Meanwhile, when the concentration data for each depth are acquired by using the gamma ray detection efficiency $\varepsilon_\gamma$ corresponding to the depth concerned, the step S205 is performed as follows.

Assuming that the gamma ray detection efficiency $\varepsilon_\gamma$ corresponding to the associated depth determined at the step S204 is $\varepsilon_{\gamma d}$, the intensity detection unit 5b determines a detection intensity of the selection gamma rays, based on the above-described equation (1) and the number A of times of detection of the selection gamma ray. The number A of times of detection used at this time is based on a result of detection of the selection gamma rays acquired (at the step S202 or by being newly selected at the step S202, for example) for the inspection target 1 by the neutron source 3 and the gamma ray detection device 5 under the same conditions as the above-described conditions including the orientation condition when the concentration data are acquired. The same detection efficiency data as that in the first embodiment are stored in the detection efficiency storage unit 8 as illustrated in FIG. 12, and the intensity detection unit 5b specifies $\varepsilon_{\gamma d}$ described above, based on the detection efficiency data in the detection efficiency storage unit 8 and the associated depth determined at the step S204, and uses the equation (1) as described above.

Next, based on the detection intensity of the selection gamma rays determined by the intensity detection unit 5b, the depth determined at the step S204, and the concentration data that are relevant to the depth concerned and that are stored in the concentration data storage unit 9b, the concentration evaluation unit 16 determines a concentration of the target component at the depth concerned.

Such concentration evaluation may be performed by a person. For example, the detection intensity, the concentration data for each depth, the associated depth, and the detection efficiency data may be displayed on a display, and a person may look at these pieces of the displayed data and determine a concentration of the target component at the associated depth.

<Variations of Inspection Method>

The following describes first to third examples as variations of the above-described nondestructive inspection method. The matters that are not described below are the same as those in the above-described nondestructive inspection method.

Figure 15A:
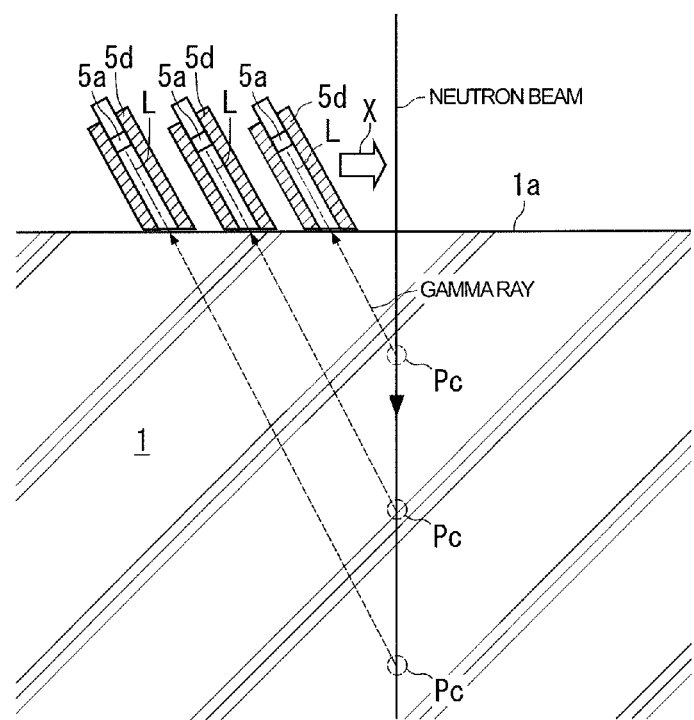
FIG. 15A is an illustration for a variation of the nondestructive inspection method.

In the first example, a plurality of sets of the gamma ray detector 5a, the intensity detection unit 5b, and the gamma ray shielding portion 5d are used. In other words, at the step S201, as in FIG. 15A, a plurality of the gamma ray detectors 5a and the neutron source 3 (not illustrated) are arranged such that the intersection positions Pc for a plurality of the gamma ray detectors 5a belonging to the respective sets are different from each other. Then, the steps S203 to S205 are performed for detection data acquired by each of the gamma ray detectors 5a at the step S202. Each time the steps S201 to S205 are thus performed, positions of a plurality of the gamma ray detectors 5a are shifted in a direction along the surface 1a (e.g., the direction of the arrow X in FIG. 15A)

at the re-started step S201, and the steps S202 to S205 are performed again, and thus, the steps S201 to S205 are repeated.

In this repetition, a neutron beam path may be fixed. In this case, in the repetition, a direction of the reference straight line L of each gamma ray detector 5a with respect to the path of the neutron beam may be fixed, or may be changed.

Figure 15B:
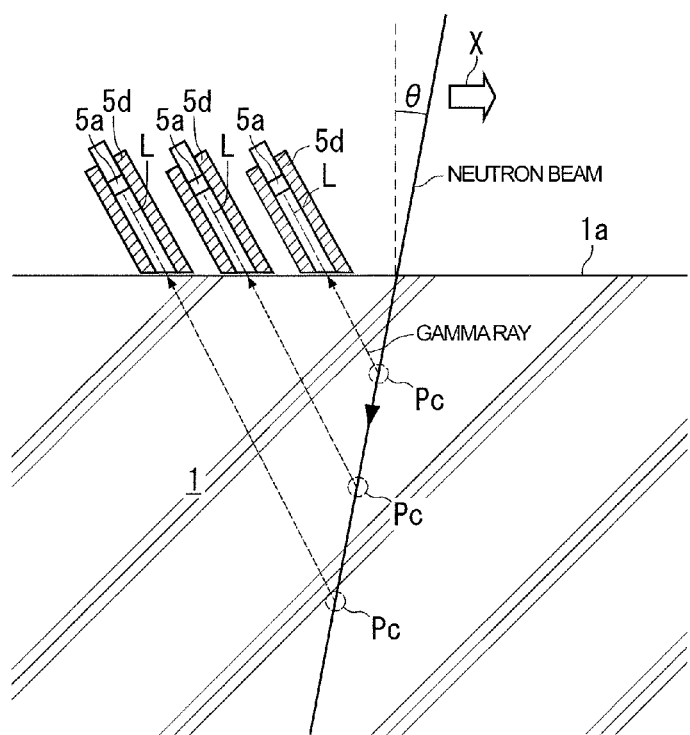
FIG. 15B is an illustration for another variation of the nondestructive inspection method.

In the second example, similarly to the first example, at the step S201, as in FIG. 15B, a plurality of the gamma ray detectors 5a and the neutron source 3 (not illustrated) are arranged such that the intersection positions Pc for a plurality of the gamma ray detectors 5a belonging to the respective sets are different from each other. Then, the steps S203 to S205 are performed for detection data acquired by each of the gamma ray detectors 5a at the step S202. Each time the steps S201 to S205 are thus performed, the neutron beam path is changed at the re-started step S201 (for example, in FIG. 15B, the path of the neutron beam is shifted in a direction of arrow X, or an incident angle θ of the neutron beam on surface 1a is changed), and the steps S202 to S205 are performed again, and thus, the steps S201 to S205 are repeated. In this repetition, the positions and orientations of a plurality of the gamma ray detectors 5a with respect to the surface 1a may be fixed.

Figure 15C:
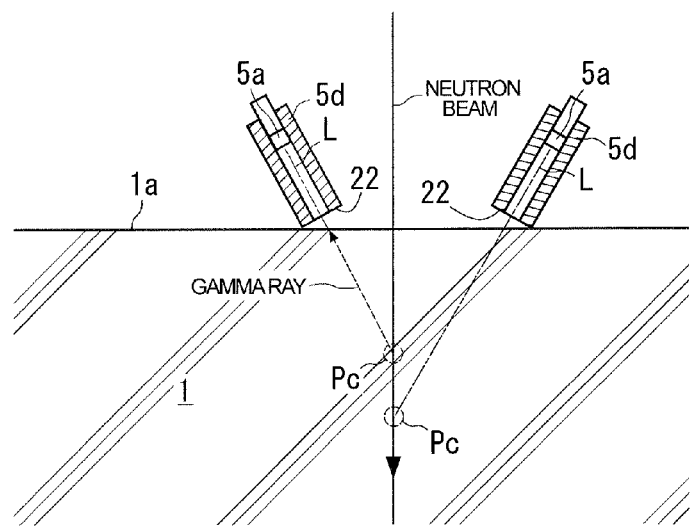
FIG. 15C is an illustration for still another variation of the nondestructive inspection method.

In the third example, as in FIG. 15C, at the step S201, a plurality of the gamma ray detectors 5a and the neutron source 3 (not illustrated) are arranged such that the intersection positions Pc for a plurality of the gamma ray detectors 5a belonging to the respective sets are different from each other. Then, the steps S203 to S205 are performed for detection data acquired by each of the gamma ray detectors 5a at the step S202. Each time the steps S201 to S205 are thus performed, an inclination of the reference straight line L of each gamma ray detector 5a relative to the surface 1a is changed at the re-started step S201, and the steps S202 to S205 are performed again, and thus, the steps S201 to S205 are repeated. In this repetition, the path of the neutron beam may be fixed.

The reference straight line L may be perpendicular to the front end face 22 as in the example of FIG. 15C. In such a case, the shape of the gamma ray shielding portion 5d described above with reference to FIG. 13A or FIG. 13B may be adopted. In the third example, one set of the gamma ray detector 5a and others may be used instead of a plurality of sets, and in this case, the other matters are the same as those described above.

In the inspection according to the first to third examples, existence or absence and a concentration of the target component can be inspected over a wide range in the inspection target 1.

The above-described third embodiment may be implemented in combination with the first embodiment or the second embodiment, or may be implemented independently of the first embodiment and the second embodiment.

Advantageous Effect of Third Embodiment

Since the gamma ray detector 5a is arranged in the gamma ray passage hole 21 of the gamma ray shielding portion 5d, the gamma ray detector 5a detects substantially only gamma rays from the depth associated with the reference straight line L of the gamma ray shielding portion 5d. For this reason, an orientation of the reference straight line L is changed, a detection intensity of the specific gamma rays is acquired for each of the orientations, and it can be determined that the target component exists at the depth associated with the orientation of the reference straight line L for which the detection intensity exceeds the set lower limit value. In this manner, a depth of the target component can be specified. When the concentration data for concentration evaluation are acquired in advance by an experiment, a concentration of the target component as well as a depth thereof can be acquired or evaluated.

The present invention is not limited to the above-described embodiment, and of course, various modifications can be made within the scope of the technical idea of the present invention. For example, each of the above-described advantageous effects does not necessarily limit the present invention. The present invention may be the invention achieving one of the advantageous effects indicated in the present specification, or may be the invention achieving another advantageous effect that can be grasped from the present specification. Any one of the following modified examples 1 to 3 may be adopted, or two or more of the modified examples 1 to 3 may be arbitrarily combined and adopted. In this case, the matters that are not described below may be the same as those described above.

Modified Example 1

In the first embodiment, the depth detection unit 11 may be omitted. In this case, based on a ratio determined at the above-described step S3 and the depth data, a person may determine a depth of the target component. For example, a ratio and depth data determined at the step S3 may be displayed on a display or be printed on a paper sheet, and a person may determine a depth of the target component while looking at the displayed or printed ratio and depth data.

Similarly, in the second embodiment, the depth detection unit 19 may be omitted. In this case, a person may determine a depth of the target component, based on a time point specified at the above-described step S103 and the depth data. For example, the time point specified at the step S103 and the depth data may be displayed on a display or be printed on a paper sheet, and a person may determine a depth of the target component while looking at the displayed or printed time point and depth data.

Modified Example 2

In the first embodiment, the concentration evaluation unit 13 may be omitted. In this case, based on a depth determined at the above-described step S4, a detection intensity of the selection gamma ray based on the gamma ray detection efficiency $\varepsilon_\gamma$ corresponding to the depth, and the above-described concentration data, a person may determine a concentration of the target component at the depth. In other words, each piece of the data (e.g., a detection intensity of the selection gamma ray detected at the step S2, the above-described detection efficiency data, a depth determined at the step S4, and the above-described concentration data) used at the above-described step S5 may be displayed on a display or be printed on a paper sheet, and a person may determine a concentration of the target component at the depth while looking at these pieces of the displayed or printed data.

Similarly, in the second embodiment, the concentration evaluation unit 14 may be omitted. In this case, based on a depth determined at the above-described step S104, a detection intensity of the selection gamma ray based on the gamma ray detection efficiency $\varepsilon_\gamma$ corresponding to the depth, and the above-described concentration data, a person may determine a concentration of the target component at the depth. In other words, each piece of the data used at the above-described step S105 may be displayed on a display or be printed on a paper sheet, and a person may determine a concentration of the target component at the depth while looking at these pieces of the displayed or printed data.

Modified Example 3

In the above-described first and third embodiments, the neutron source 3 is not limited to a neutron source using an accelerator including a pulse type as long as the neutron source 3 can make a neutron beam incident on the inspection target 1. For example, the neutron source 3 may be an RI radiation source (e.g., $^{252}$Cf) or a DD or DT neutron generator tube that generates neutrons. When the RI radiation source is used, for example, in FIG. 1 and FIG. 12, the RI radiation source is arranged at a position of the target 3d, and the container 3e surrounding the RI radiation source is provided, and the container 3e is provided with the tubular shielding member 3f for the RI radiation source.

The present invention is not limited to the above-described embodiments, embodied examples, and modified examples, and can be widely applied without departing from the essence of the invention. For example, the above-described selection gamma ray is not limited to the above-described example as long as the selection gamma ray is the specific gamma ray.

REFERENCE SIGNS LIST 1 inspection target; 1a surface; 3 neutron source; 3a ion source; 3b acceleration device; 3c beam adjuster; 3d target; 3e container; 3f tubular shielding member; 3g moderator; 5 gamma ray detection device; 5a gamma ray detector; 5b intensity detection unit; 5c data acquisition unit; 5d gamma ray shielding unit; 7 ratio calculation unit; 8 detection efficiency storage unit; 9a, 9c depth data storage unit; 9b concentration data storage unit; 10, 20 nondestructive inspection apparatus; 11 depth detection unit; 13, 14, 16 concentration evaluation unit; 15 time-point specifying unit; 17 cooling device; 18 hole; 19 depth detection unit; 21 gamma ray passage hole; 21a opening; 22 front end surface; 23, 24 shielding block; L reference straight line; Pc intersection position

The invention claimed is:

1. A nondestructive inspection apparatus for determining a depth of chlorine that may exist in a concrete structure including reinforcing steel bars whose corrosion can be caused by chlorine, the nondestructive inspection apparatus comprising:
a neutron source that emits a neutron beam including at least fast neutrons to a surface of a concrete structure including reinforcing steel bars and corrosive chlorine Cl;
a gamma ray detection device configured so as to detect intensities of a plurality of types of specific gamma rays, based on respective different specific energies of the plurality of types of specific gamma rays that are generated from the chlorine Cl in the concrete structure due to the neutron beam; and
a ratio calculation unit that receives, from the gamma ray detection device, the detected intensities of the plurality of types of specific gamma rays, and calculates as an index value indicative of a depth of the chlorine Cl within the concrete structure, a ratio between the detected intensities of the plurality of types of specific gamma rays.

2. The nondestructive inspection apparatus according to claim 1, further comprising:
a storage device including at least one storage area;
a data storage unit that is a storage area in the storage device and stores depth data representing a relation between a depth, at which the chlorine Cl exists in the concrete structure, and a ratio between detected intensities of the plurality of types of specific gamma rays; and
a depth detection unit that determines the depth, based on the depth data stored in the data storage unit and the ratio calculated by the ratio calculation unit.

3. The nondestructive inspection apparatus according to claim 2, further comprising:
another storage device including at least one storage area;
a concentration data storage unit that is a storage area in the storage device or in the another storage device and stores, for each depth in the concrete structure, concentration data representing a relation between a detected intensity of a selection gamma ray that is one of the plurality of types of specific gamma rays and a concentration of the chlorine Cl; and
a concentration evaluation unit that determines a concentration of the chlorine Cl at the determined depth, based on the determined depth, the concentration data stored in the concentration data storage unit, and the detected intensity of the selection gamma ray.

4. The nondestructive inspection apparatus according to claim 2, wherein the depth detection unit determines the depth, only by applying the ratio to the depth data.

5. The nondestructive inspection apparatus according to claim 1, wherein the neutron source emits a temporally continuous or pulsed neutron beam.

6. A nondestructive inspection method for determining a depth of chlorine that may exist in a concrete structure including reinforcing steel bars whose corrosion maybe caused by chlorine, the nondestructive inspection method comprising:
an emission step of emitting a neutron beam including at least fast neutrons to a surface of a concrete structure including reinforcing steel bars and corrosive chlorine Cl;
a gamma ray detection step of detecting intensities of a plurality of types of specific gamma rays, based on respective different specific energies of the plurality of types of specific gamma rays that are generated from the chlorine Cl in the concrete structure due to the neutron beam; and
a ratio calculation step of calculating, as an index value indicative of a depth of the chlorine Cl in the concrete structure, a ratio between the detected intensities of the plurality of types of specific gamma rays.

7. The nondestructive inspection method according to claim 6, further comprising:
a depth detection step of determining the depth, based on depth data and the ratio calculated at the ratio calculation step,
wherein the depth data represents a relation between a depth, at which the chlorine Cl exists in the concrete structure, and a ratio between detected intensities of the plurality of types of specific gamma rays.

8. The nondestructive inspection method according to claim 7, further comprising:
a concentration evaluation step of determining a concentration of the chlorine Cl at the determined depth, based on the determined depth, a detected intensity of one of the plurality of types of specific gamma rays, and concentration data representing a relation between a detected intensity of the one of the plurality of types of specific gamma rays and a concentration of the chlorine Cl for each depth in the concrete structure.

9. A nondestructive inspection apparatus for inspecting concrete structures including reinforcing steel bar, the nondestructive inspection apparatus comprising:
a neutron source that emits a pulsed neutron beam including at least fast neutrons to a surface of a concrete structure including reinforcing steel bars and corrosive chlorine Cl, and thereby makes the at least fast neutrons incident on the surface of the concrete structure;
a gamma ray detection device that detects gamma rays including a specific gamma ray generated from the chlorine Cl in the concrete structure due to the pulsed neutron beam, detects an energy spectrum of the detected gamma rays at each time point, and generates time-difference-to-spectrum data, in which each time point is associated with the detected energy spectrum of the gamma rays detected at each time point;
a time-point specifying unit that specifies, in a relation to a reference time point, a time point, at which the specific gamma ray is detected, based on the time-difference-to-spectrum data generated by the gamma ray detection device; and
a depth detection unit that determines a depth of the chlorine Cl within the concrete structure, based on the time point specified by the time-point specifying unit.

10. The nondestructive inspection apparatus according to claim 9, further comprising:
a storage device including at least one storage area; and
a depth data storage unit that is a storage area in the storage device and stores depth data representing a relation between a depth, at which the chlorine Cl exists in concrete structure, and a time point, at which the specific gamma ray is detected when the pulsed neutron beam is made incident on the concrete structure,
wherein the depth detection unit determines the depth, based on the depth data stored in the depth data storage unit and the time point specified by the time-point specifying unit, and
the pulsed neutron beam includes thermal neutrons.

11. The nondestructive inspection apparatus according to claim 10, further comprising:
another storage device including at least one storage area;
a concentration data storage unit that is a storage area in the storage device or in the another storage device and stores, for each depth in the concrete structure, concentration data representing a relation between a detected intensity of the specific gamma ray and a concentration of the chlorine Cl; and
a concentration evaluation unit that determines a concentration of the chlorine Cl at the determined depth, based on the determined depth, the concentration data stored in the concentration data storage unit, and an intensity of the specific gamma ray detected by the gamma ray detection device.

12. A nondestructive inspection method for a concrete structure including reinforcing steel bars, the nondestructive inspection method comprising:
an emission step of emitting a pulsed neutron beam including at least fast neutrons to a surface of a concrete structure including reinforcing steel bars and corrosive chlorine Cl, and thereby making the at least fast neutrons incident on the surface of the concrete structure;
a gamma ray detection step of detecting a specific gamma ray generated from the chlorine Cl in the concrete structure due to the pulsed neutron beam;
a time-point specifying step of specifying, in a relation to a reference time point, a time point, at which the specific gamma ray is detected; and
a depth detection step of determining a depth of the chlorine Cl, based on the time point specified at the time-point specifying step.

13. The nondestructive inspection method according to claim 12,
wherein the gamma ray detection step detects the specific gamma ray having a specific energy and generated from the chlorine Cl in the concrete structure due to the pulsed neutron beam, and
the time-point specifying step specifies, in the relation to the reference time point, the time point, at which the specific gamma ray is detected, based on a number of times of a detection of the specific gamma ray at each time point.

14. A nondestructive inspection apparatus for emitting, to an inspection target, a neutron beam including at least fast neutrons, detecting and identifying a specific gamma ray generated due to the neutron beam, and determining a depth, at which a target component exists, based on a result of detecting and identifying the specific gamma ray generated due to the neutron beam, the nondestructive inspection apparatus comprising:
a neutron source that emits a neutron beam to a surface of an inspection target; and
a gamma ray detection device that detects a specific gamma ray generated due to the neutron beam incident on the inspection target,
wherein the gamma ray detection device includes a gamma ray detector for detecting the specific gamma ray, and a gamma ray shielding portion comprising a gamma ray passage hole, the gamma ray passage hole includes an opening, through which gamma rays are allowed to enter, the gamma ray detector is arranged in the gamma ray passage hole so as to be at a position shifted to a deep side from the opening, and the opening and the gamma ray detector are positioned on a reference straight line,
the gamma ray shielding portion includes a gap and two shielding blocks separated by the gap from each other, and the gap is the gamma ray passage hole,
the gap extends along the reference straight line, and
a size of the gap in a first direction perpendicular to the reference straight line is smaller than a size of the gap in a second direction perpendicular to both the reference straight line and the first direction.

15. The nondestructive inspection apparatus according to claim 14, wherein the gamma ray shielding portion includes a front end surface, on which the opening is formed, and the front end surface is formed such that the reference straight line extends obliquely relative to the front end surface.

16. The nondestructive inspection apparatus according to claim 14, wherein the gamma ray detection device detects the specific gamma ray based on a specific energy of the specific gamma ray that is generated by a reaction of the neutron beam with a the target component in the inspection target.

* * * * *